(12) United States Patent
Imran

(10) Patent No.: US 10,220,144 B2
(45) Date of Patent: Mar. 5, 2019

(54) APPARATUS, SYSTEMS AND METHODS FOR THE TREATMENT OF NEUROLOGICAL CONDITIONS

(71) Applicant: InCube Labs, LLC, San Jose, CA (US)

(72) Inventor: Mir A. Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 482 days.

(21) Appl. No.: 13/684,118

(22) Filed: Nov. 21, 2012

(65) Prior Publication Data

US 2014/0074060 A1  Mar. 13, 2014

Related U.S. Application Data

(60) Provisional application No. 61/562,435, filed on Nov. 21, 2011.

(51) Int. Cl.
*A61M 5/172* (2006.01)
*A61M 5/142* (2006.01)
(Continued)

(52) U.S. Cl.
CPC ....... *A61M 5/1723* (2013.01); *A61B 5/04001* (2013.01); *A61M 5/14276* (2013.01);
(Continued)

(58) Field of Classification Search
CPC ........ A61M 5/1723; A61M 2005/1726; A61B 5/0478; A61B 5/4094; A61B 5/4839;
(Continued)

(56) References Cited

U.S. PATENT DOCUMENTS 5,237,996 A   8/1993  Waldman et al.
5,551,426 A   9/1996  Hummel et al.
(Continued)

FOREIGN PATENT DOCUMENTS

WO   WO 2008/068759   6/2008
WO   WO 2010/085782   7/2010

OTHER PUBLICATIONS

International Search Report, Written Opinion, and Notice of Transmittal of Same dated Aug. 26, 2010 in International App. PCT/US2010/022051.
(Continued)

*Primary Examiner* — Amber Stiles
(74) *Attorney, Agent, or Firm* — Mahamedi IP Law LLP; Joel Harris

(57) ABSTRACT

Various embodiments described herein provide an apparatus system, and method for detecting and treating various neurological events or conditions such as epilepsy and migraine headaches which are associated with cortical spreading depression (CSD). Also, many embodiments provide an apparatus, system and method for delivery of a drug such as a loop diuretic to prevent or reduce the duration of a seizure or other event associated with CSD. The drug may delivered intra-cranially in a dose selected to produce a localized effect in the brain to prevent or reduce the duration of the seizure or other event while minimizing adverse peripheral effects such as diuresis or electrolyte loss.

37 Claims, 25 Drawing Sheets

(51) Int. Cl.
*A61B 5/04* (2006.01)
*A61N 1/36* (2006.01)

(52) U.S. Cl.
CPC .............. *A61M 2005/1726* (2013.01); *A61M 2210/0693* (2013.01); *A61N 1/36064* (2013.01)

(58) Field of Classification Search
CPC .. A61B 5/4836; A61N 1/0529; A61N 1/0534; A61N 1/0536; A61N 1/0539
USPC ....................................... 604/503; 607/3, 45
See application file for complete search history.

(56) References Cited

U.S. PATENT DOCUMENTS

| | | | |
|---|---|---|---|
| 5,713,923 A * | 2/1998 | Ward | A61M 5/14276 128/899 |
| 6,016,449 A | 1/2000 | Fischell et al. | |
| 6,353,762 B1 | 3/2002 | Baudino et al. | |
| 7,006,859 B1 | 2/2006 | Osorio et al. | |
| 7,181,288 B1 | 2/2007 | Rezai et al. | |
| 7,831,308 B2 | 11/2010 | Rezai et al. | |
| 8,374,703 B2 | 2/2013 | Imran | |
| 8,467,877 B2 * | 6/2013 | Imran | 607/45 |
| 2002/0062143 A1 | 5/2002 | Baudino et al. | |
| 2004/0199235 A1 | 10/2004 | Younis | |
| 2005/0182453 A1 | 8/2005 | Whitehurst et al. | |
| 2006/0025387 A1 * | 2/2006 | Hochman | A61K 31/19 514/165 |
| 2006/0122677 A1 * | 6/2006 | Vardiman | A61N 1/0534 607/116 |
| 2007/0060973 A1 | 3/2007 | Ludvig et al. | |
| 2007/0149526 A1 * | 6/2007 | Hochman | A61K 31/34 514/237.8 |
| 2007/0150024 A1 * | 6/2007 | Leyde | A61B 5/0476 607/45 |
| 2007/0150025 A1 | 6/2007 | Dilorenzo et al. | |
| 2007/0186923 A1 * | 8/2007 | Poutiatine | A61J 7/0038 128/200.14 |
| 2009/0317387 A1 * | 12/2009 | Paton | A61K 39/39558 424/133.1 |
| 2010/0063071 A1 * | 3/2010 | Kiesman | A61K 9/0019 514/263.24 |
| 2010/0191305 A1 * | 7/2010 | Imran | A61B 5/04004 607/45 |

OTHER PUBLICATIONS

Non-Final Office Action dated Dec. 29, 2011 in U.S. Appl. No. 12/359,830.
Non-Final Office Action dated May 22, 2012 in U.S. Appl. No. 13/301,584.
International Preliminary Report on Patentability dated Aug. 4, 2011 in PCT/US2010/022051.
Office Action dated Apr. 3, 2013 in Chinese Application 201080008430.8.
First Examination Report dated Aug. 27, 2013 in Australian Application No. 2010206520.
Notice of Allowance dated Feb. 5, 2013 in U.S. Appl. No. 13/301,584.
Non-Final Office Action dated Oct. 8, 2013 in U.S. Appl. No. 13/917,627.
Notice of Allowance dated Sep. 17, 2012 in U.S. Appl. No. 12/359,830.

* cited by examiner

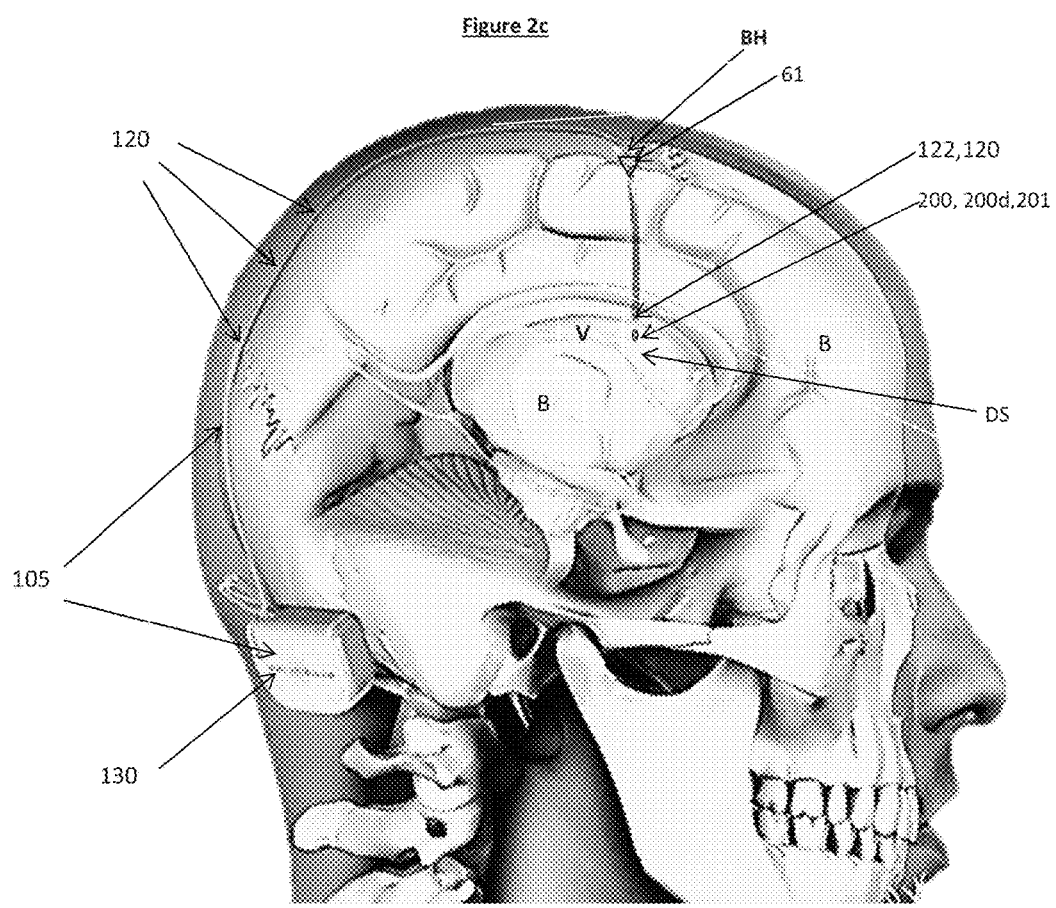

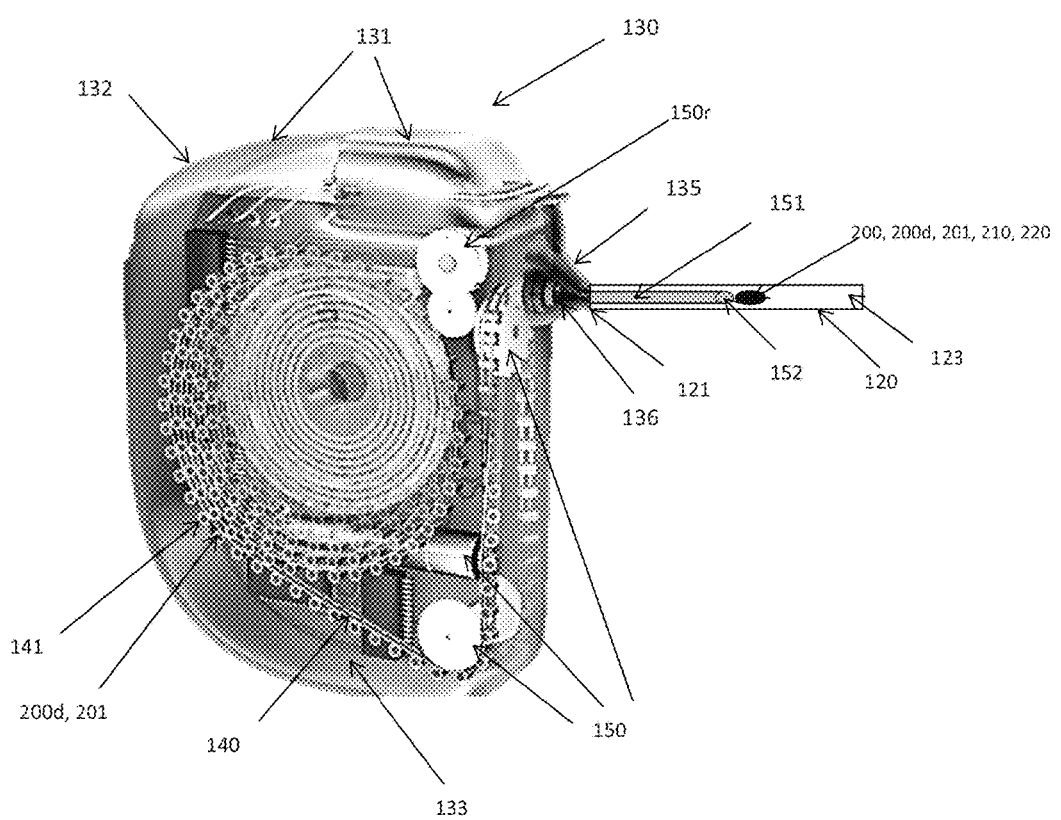

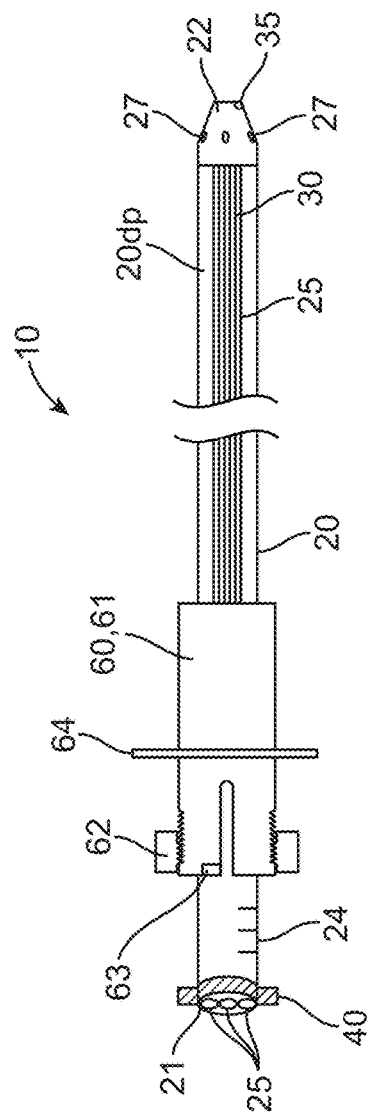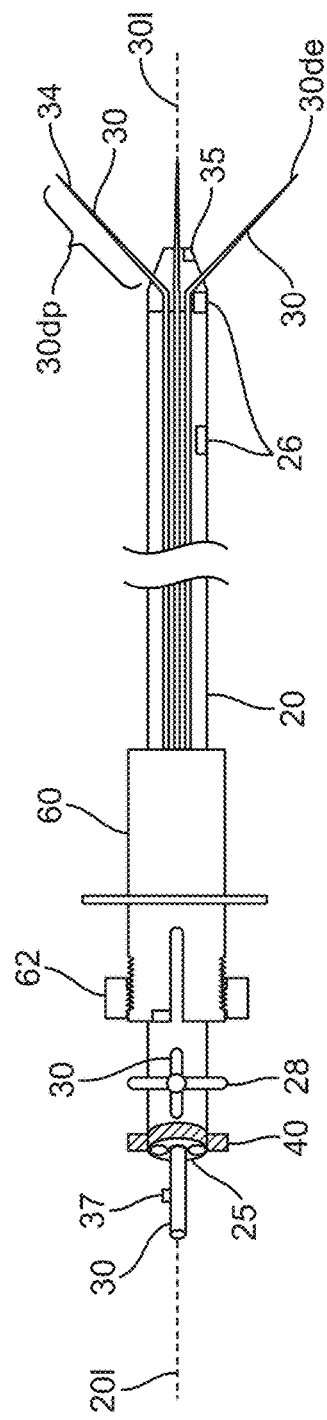
FIG. 6a
FIG. 6b

Normal Brain Activity

Brain Activity During a
Pre-Seizure or Seizure Event

APPARATUS, SYSTEMS AND METHODS FOR THE TREATMENT OF NEUROLOGICAL CONDITIONS

RELATED APPLICATIONS

This application claims the benefit of priority to U.S. Provisional Patent Application No. 61/562,435, entitled "METHOD FOR THE DETECTION AND TREATMENT OF ABERRANT NEURAL-ELECTRIC ACTIVITY," filed Nov. 21, 2011; the aforementioned application is hereby incorporated by reference herein in its entirety for all purposes.

This application is also a continuation-in-part U.S. patent application Ser. No. 12/359,830, entitled "METHOD AND APPARATUS FOR THE DETECTION OF ABERRANT NEURAL-ELECTRIC ACTIVITY," filed Jan. 26, 2009; the aforementioned application is hereby incorporated by reference herein in its entirety for all purposes.

FIELD OF THE INVENTION

Embodiments described herein relate to an apparatus, system and method for the detection and treatment of adverse neurological events or conditions. More specifically, embodiments described herein relate to an apparatus and methods for the detection and treatment of neurological events or conditions characterized or associated with aberrant neurological activity and/or cortical spreading depression.

BACKGROUND

There are a number of neurological events and conditions which are characterized by abnormal neural-electric activity in the brain including epilepsy, migraine headaches and even some forms of depression. Epilepsy is a disease characterized by recurrent unprovoked seizures which result in episodic impairment or loss of consciousness, abnormal motor phenomena, psychic or sensory disturbances, or the perturbation of the autonomic nervous system. It is caused by abnormal firing of neurons in the brain, a condition known as epileptogenesis. These abnormal firings or electrical discharges may start in small neuronal populations (these are known as epileptogenic foci, the condition defined as focal epilepsy) or much larger areas of the brain (this condition is defined as generalized epilepsy). Often there can be a period of abnormal firing of neurons which precedes the full blown seizure. This period is known as a pre-seizure state and it can include one or more events of abnormal firing, known as pre-seizure events.

Whatever the cause, the human and financial impact of the disease is significant. The prevalence of epilepsy in the US is currently about three million worldwide; about fifty million with 200,000 new cases are diagnosed each year in the US alone. Ten percent of the American population will experience a seizure in their lifetimes. Due to the impairing nature of epileptic seizures, the disease can prevent patients from performing a number of routine activities including driving a car or operating machinery. Many states put driving restrictions on those diagnosed with epilepsy. In a sub-population of patients, the severity of the disease is so extreme that they are essentially incapacitated. The economic cost of the disease is estimated to be $12.5 billion per year in direct and indirect costs.

While there are a number of available drug therapies, these therapies have a number of side effects including hyperplasia, slurred speech and memory loss. They also require precise control of the therapeutic dosage to avoid occurrence of seizures for too low a dose or side effects for too high a dose. Also estimates are that at least 20-30 percent of epilepsy patients cannot be effectively treated with currently available drug therapies. Many persons having medically refractory epilepsy with partial-onset seizures are known not to respond well to anti seizure medication. The only option for these and other patients is radical brain surgery which presents significant mortality issues. While there have been various attempts at using electrical stimulation of the brain, particularly deep brain stimulation as a means of treating the disease, these approaches are limited to the use of continuous stimulation and do not employ detection means so as to modulate or otherwise modify the stimulation causing a change in the patient's brain activity. Also continuous deep brain stimulation has several drawbacks. To be effective, the treatment may require stimulation of the neocortex, which is often the origin or focus of epileptic seizures. However, continuous or frequent stimulation in this region may cause various neurological symptoms including speech impairment, sensory impairment, involuntary motion, memory loss and depression. Also the foci can originate in a number of areas of the brain, not just the neocortex, including the cerebral cortex, primary motor cortex, and premotor cortex hippocampus, to name a few. Thus, stimulating only the neocortex may not be effective.

While several approaches have been employed for the localization of epileptic foci using electroencephalogram measurements (EEG), these have largely relied on surface electrodes, which also have drawbacks. These include very weak signals when epileptogenic foci are located in deep brain tissue, when there are two or more foci which can cancel each other out (due to the dipole nature of the signal) or closed field foci (due to the foci being located in a sheet of non-parallel tissue. Other drawbacks with surface electrodes include the tendency of the various tissue layers which overly the foci (e.g., the meninges, bone, skin, etc.) to spread out the signal over a larger layer of the scalp making localization difficult and the fact that dipoles generated by the foci can be oriented parallel or obliquely to the electrodes causing phase reversal and false localization of the signal. Many of these same issues, including difficulties in localization and phase reversal, can also occur for an implanted electrode. These issues can make detection of pre-seizure events leading to a seizure even more difficult since the magnitude and duration of aberrant neural-electric activity during the pre-seizure event can be reduced compared to an actual seizure.

Accordingly, a need exists for devices and methods for detecting seizure or pre-seizure events/states so that acute treatment (e.g., drug or stimulation) can be delivered to prevent the seizure and/or minimize its effects.

BRIEF DESCRIPTION OF THE DRAWINGS

FIG. 2c is a side view illustrating an embodiment of a system for the intracranial delivery of a drug other therapeutic agent to the patient's brain.

FIG. 2d is a side view illustrating an embodiment of a drug storage and delivery device which may be used in the embodiment of FIG. 2c.

FIGS. 4a-4b are perspective views and FIG. 4c is a frontal cross-sectional view.

FIG. 6a is side view showing an embodiment of the ANEA detection apparatus with the electrode members in the non deployed state inside the introducer.

FIG. 6b is side view showing an embodiment of the ANEA detection apparatus with the electrode members in advanced out of the introducer in a deployed state.

FIG. 8a shows an embodiment of an electrode having an abrupt bend, FIG. 8b shows an embodiment having a curved bend.

FIG. 10a illustrates an electrode member having a solid conductive core, while FIG. 10b illustrates an electrode member having at least one lumen.

FIG. 16a shows the burr hole opening in the skull. FIG. 16b shows placement of a burr hole plug in the burr hole opening. FIG. 16c shows the introduction and advancement of the introducer through the burr hole plug. FIG. 16d shows the full advancement of the introducer. FIG. 16e shows the deployment of the electrode members to a configuration for detecting the Foci.

FIG. 17a is over a period of normal activity and FIG. 17b is over a period of aberrant neural-electric activity in the brain.

DETAILED DESCRIPTION OF THE INVENTION

Figure 1:
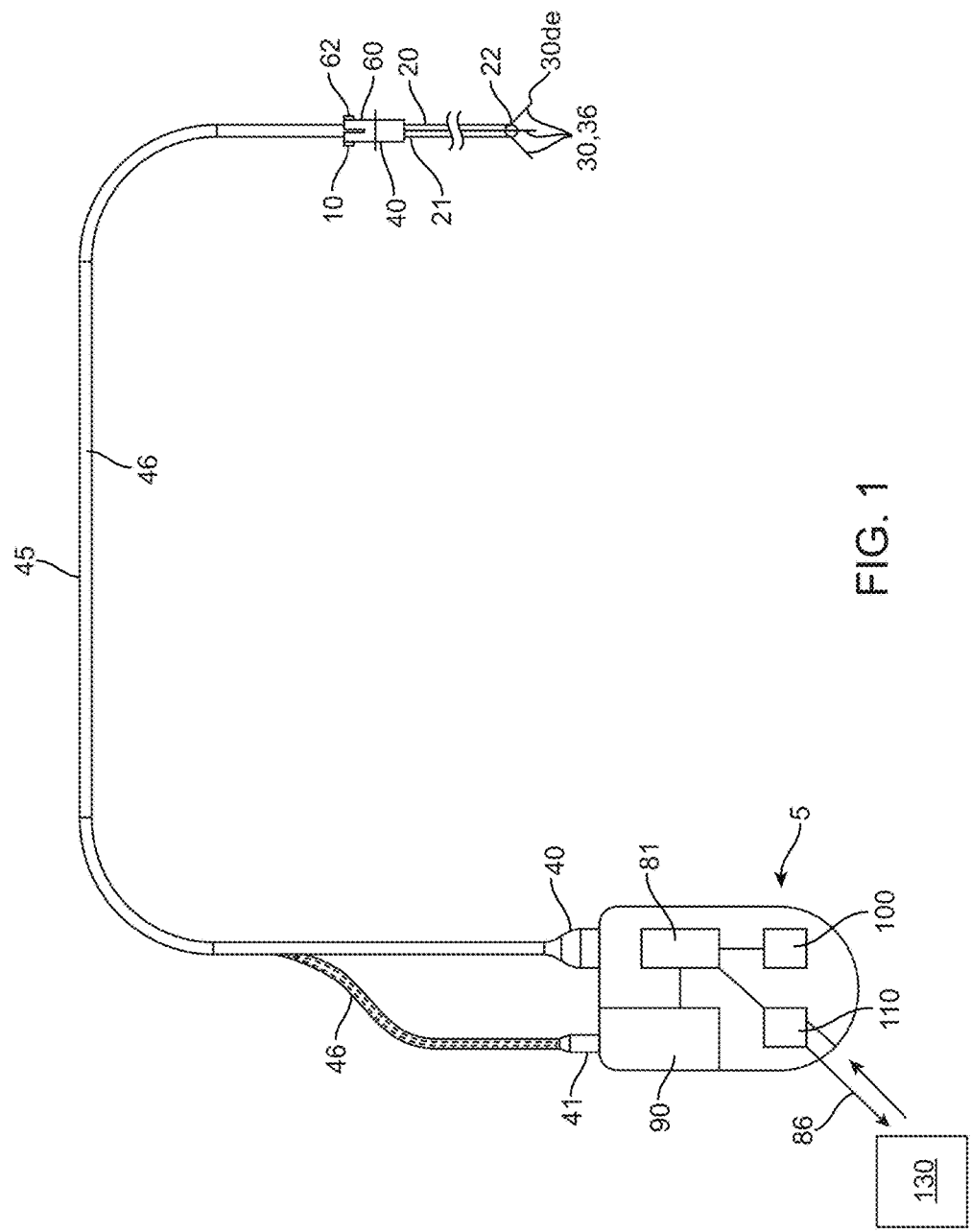
FIG. 1 is a plan view of an embodiment of a system and apparatus for detection of aberrant neural-electric activity (ANEA).

Various embodiments described herein provide a system, apparatus and method for detecting and treating various neurological events or conditions such as epilepsy and migraine headaches. Many embodiments provide an apparatus and method for detecting aberrant activity such as aberrant neurological activity and/or cortical spreading depression (CSD) prior to the actual physical manifestation of the event or condition caused by the aberrant activity (e.g., detect the electrical activity and/or CSD prior to occurrence of an epileptic seizure, migraines or other neurological event or condition) and then use that information to initiate the delivery of a drug to prevent or reduce the duration of the seizure or other neurological event. Also, many embodiments provide an apparatus system and method for the intracranial delivery of one or more drugs to various regions within the brain. Such drugs may be so delivered to prevent or reduce the duration of an epileptic seizure, migraine headaches or other neurological condition by preventing, slowing or reducing the duration of aberrant neurological activity and/or a wave of cortical spreading depression.

In an embodiment, an apparatus is implanted at least partially in the brain that includes suitably oriented electrode members that are configured to be able to detect and locate the direction of aberrant neural-electric activity in the brain. Specific embodiments can detect and interpret an electric field generated by a foci or other origin of aberrant neural-electric activity. In an embodiment, such information is determined and interpreted as a marker to the onset of an epileptic seizure or other neurological event or condition.

In one or more embodiments, the marker of the onset of an epileptic seizure or other neurological event or condition can be used to control the delivery of a therapeutically effective amount of a drug, such as an ion co-transporter antagonist to block, slow or reduce the duration of the aberrant neuron-electric activity and/or the duration of a wave of cortical spreading depression so as to prevent or reduce the duration of the seizure. In one or more embodiments, the ion co-transporter antagonist may correspond to a cation-chloride co-transporter antagonist. Still more specifically, the cation-chloride co-transporter antagonist may correspond to a loop diuretic such as furosemide and/or its analogues and derivatives.

Still further, embodiments described herein provide for detection of aberrant neural-electric activity (ANEA) in a brain of a patient that is likely to cause an epileptic pre-seizure event or a seizure event. In an embodiment, an electric field that is caused or otherwise associated by the ANEA is detected from inside the brain or skull of the patient. An electric field vector characteristic is determined from the electric field. The electric vector is interpreted as being a marker to epileptic pre-seizure event or seizure event. The marker may correspond to a characteristic that is likely to be a precursor to the seizure. According to one or more embodiments, detecting the electrical field may be in the form of detecting voltage (or current) on electrodes that are in the skull or brain at the time of ANEA. The marker may be then used to deliver a therapeutically effective dose.

Figure 2A:
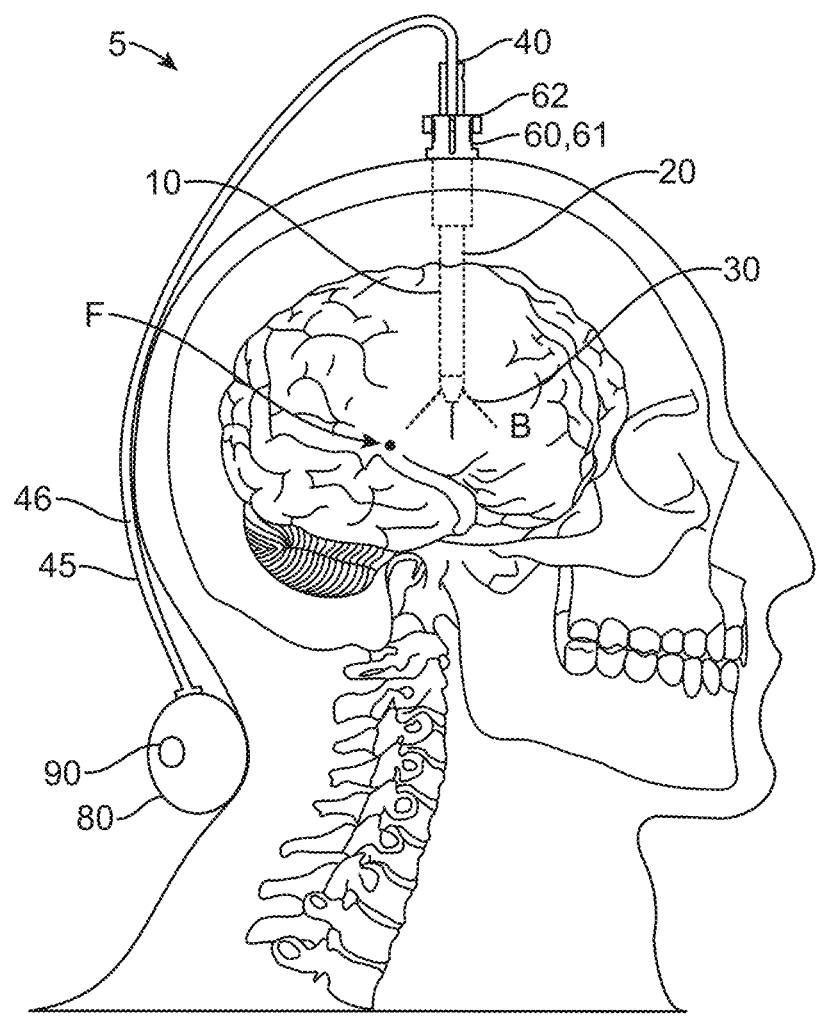
FIG. 2a is a side view showing placement and use of the system and apparatus from the embodiment of FIG. 1 to detect aberrant neural-electric activity in the brain.
Figure 2B:
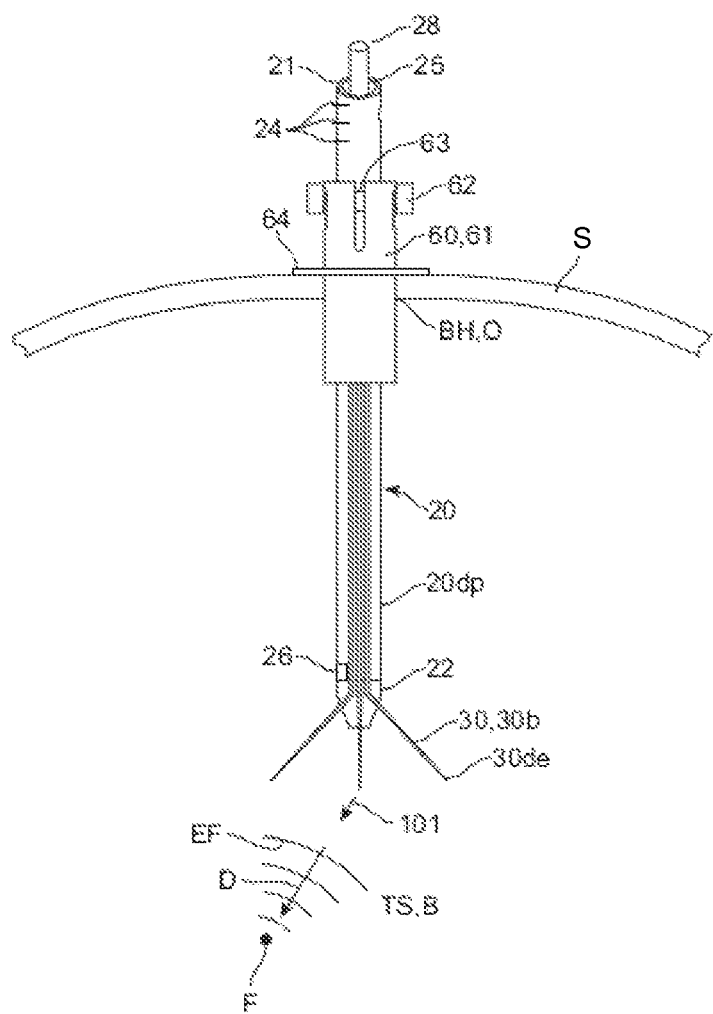
FIG. 2b is a side view showing placement of the plug in burr hole in the skull and the introduction of the ANEA detection apparatus at tissue site in the brain.
Figure 3:
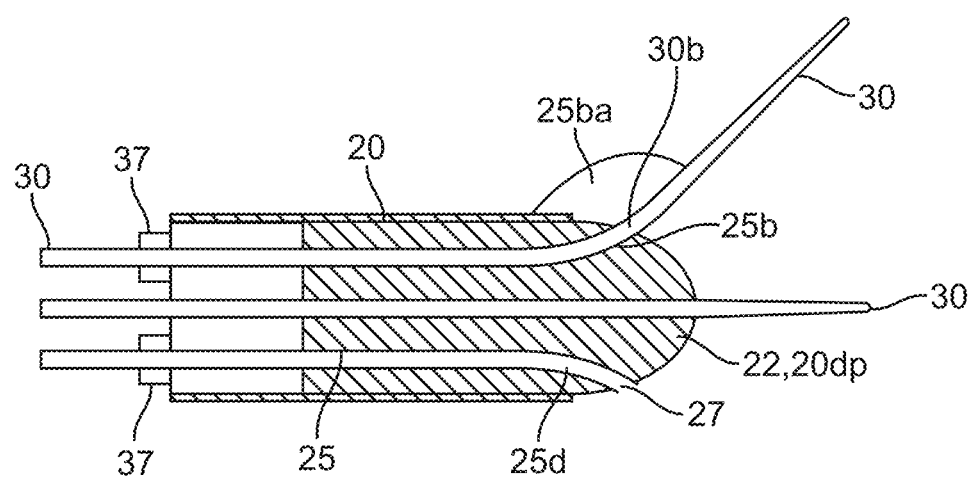
FIG. 3 is cut away side view of a distal portion of the deployed electrode members illustrating use of bent lumens in the introducer to deflect electrode members.
Figure 4A:
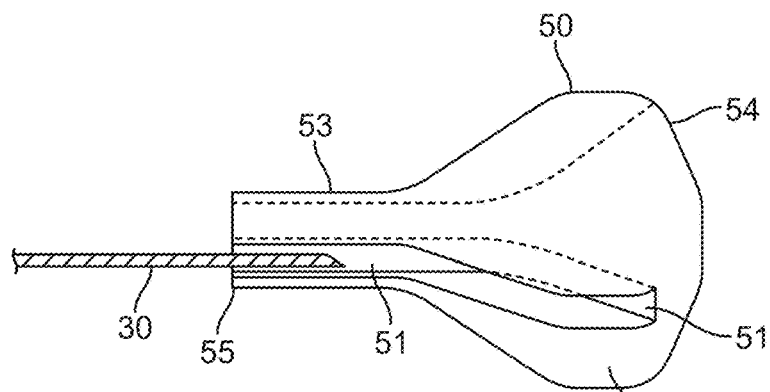
FIGS. 4a-4c are various views showing embodiments of a deflection fixture positioned within the introducer to deflect the electrode members.
Figure 4B:
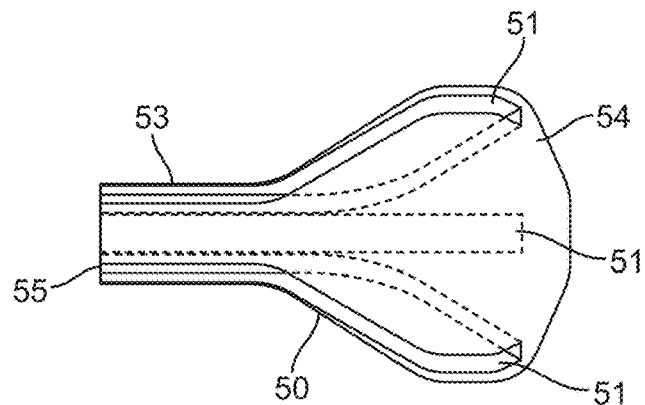
Figure 4C:
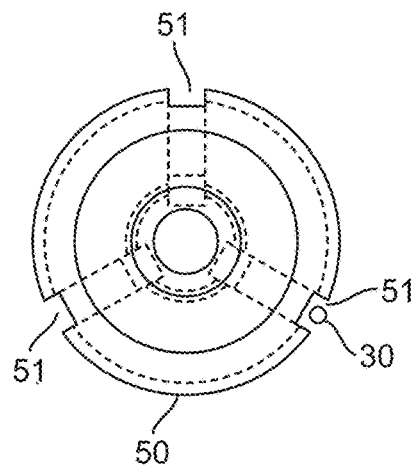
Figure 5:
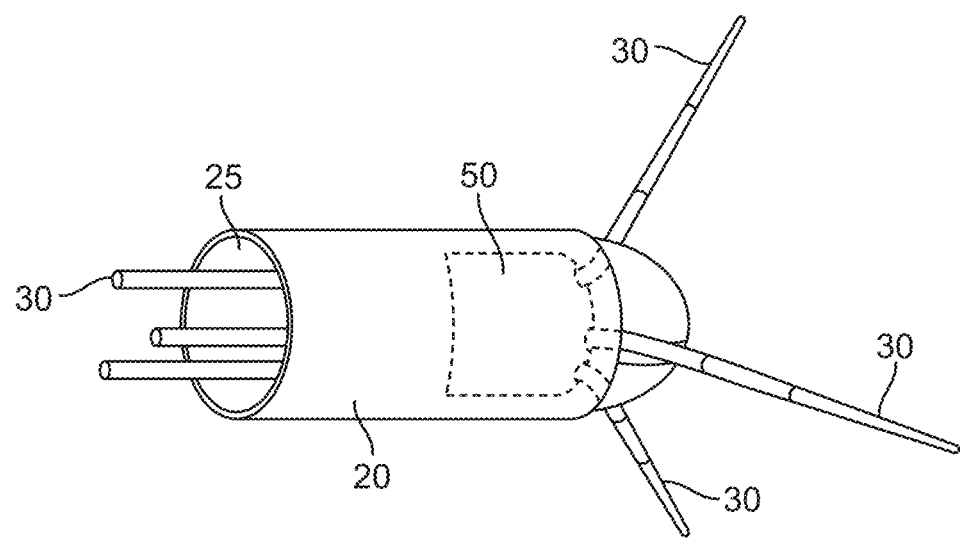
FIG. 5 is a perspective view showing the electrode members existing from the deflector.

Referring now to FIGS. 1-3, various embodiments provide for a system 5 and apparatus 10 for detection of aberrant neural-electric activity (ANEA) and/or cortical spreading depression. System 5 comprises apparatus 10 and a control module 80 described herein. Apparatus 10 includes an introducer 20 having one or more lumens 25, a reference electrode 35 and a plurality of electrode members 30 which are advanceable in lumens 25 to be deployed into brain tissue. Electrode members 30 have a non-deployed state when positioned in the introducer and a deployed state when advanced out of the introducer. In the deployed state, the electrode members can have a bent shape 30B. This bent shape can be used to define a detection volume DV for detection of a Foci F of ANEA.

Introducer 20 has proximal and distal ends 21 and 22 and is configured to be inserted into the skull S of a patient so as to position the electrode members 30 at a target tissue site TS in the brain B. Proximal end 21 can be configured to be coupled to one or more electrical, fluidic or other connectors 40. Embodiments of electrical connectors 40 can include standard connectors such as USB and Firewire connectors and can be configured to be coupled to external processors, A/D converters and like circuitry. Connectors 40 can also comprise a communication port such as an RF or infrared port. In many embodiments, connector 40 is configured to be coupled to external control module 80. In these and related embodiments, connector 40 can be coupled to module 80 via a connecting member 45 which can include electrical wiring and one or more lumens 46 for delivery of fluids including drug containing fluids as well as solids. In one or more embodiments, member 45 may correspond to a catheter, such as a type used for CSF shunts and may be configured to be implanted subcutaneously under the patient's scalp.

In various embodiments, introducer 20 can be configured to be directly introduced into brain tissue through an opening O in the skull S, or it can be introduced via means of a plug or other skull portal device 60 such as a burr hole plug 61 which is configured to be placed and secured into a burr hole BH (as shown in FIGS. 2a and 2b). Typically, plug 60 includes a locking device 62 such as a clamp or other fixation mechanisms which lock or fix introducer 20 to the plug 60 so that introducer 20 does not move after insertion. Introducer 20 can also be stabilized by a flange 64 on plug 60 (or other suitable structure or mechanism). One or more of the plug, introducer or locking device can contain a sensor 63 to detect movement of the introducer or otherwise detect an unlocked state of the introducer or if it has otherwise become loose. Suitable sensors 63 include contact sensors, hall effect switches, accelerometers and like devices. Sensors 63 can be coupled to circuitry in control module 80 discussed herein to alert the patient or medical care giver if introducer 20 is no longer in a fixed state. This circuitry can include various filters (e.g., low pass, high pass, etc.) to filter out movement attributed to normal head and body motion from movement attributed to the loosening of introducer 20 from the locking device 62.

Distal introducer end 22 may be configured with a tapered, or other related shape and can be tissue penetrating to facilitate introduction into brain tissue. The introducer may also be configured to track over a guide wire (not shown) which is advanced through a lumen 25 so as to facilitate placement of the distal end 22 at a selected target tissue site TS in the brain. Placement at the target site TS can also be facilitated by use of one or more radio-opaque or echogenic markers 26 which can be positioned at one or more locations on the introducer including distal end 22. Markers 26 allow the introducer to be advanced under fluoroscopic observation or other imaging modality. All or a portion of introducer 20 can comprise various biocompatible polymers known in the art including, without limitation, polyethylene, PET, PEBAX, PTFE, silicone, polyurethane and combinations thereof. These materials can also comprise one or more radio-opaque materials known in the art, including titanium dioxide.

As shown in greater detail by FIG. 3, introducer 20 includes one or more lumens 25, which can be configured for advancement of electrode members 30, guide-wires, viewing scopes, lights sources and like devices. Lumens 25 can also be configured for providing suction as well as infusion of various solutions including one or more medicaments solutions (e.g., a solution containing a loop diuretic, such as furosemide) for treatment of epilepsy, migraines and other brain related conditions and diseases. Each lumen 25 can also include a port 27 positioned at distal portion 20*dp* of introducer to allow for the passage of electrode member 30, as well as fluids and medicaments. In many embodiments, the introducer can include separate lumens 25 for each electrode member 30. This allows for independent advancement of electrode members 30. As is discussed herein, in many embodiments, the distal portion of members 30 can include a bend or curve 30*b*. This can be achieved by configuring the distal portion 25*d* of lumens 25 to have an internal bend 25*b* which can correspond to the amount of bend in member 30. In various embodiments, the angle 25*ba* of bend 25*b* can be in the range from 20 to 90°, with specific embodiments of 30, 40, 45, 50, 60, 70 and 80°.

Referring now to FIGS. 4A, 4B, 4C and 5, one or more embodiments provide that all or a portion of electrode members 30 are advanceable in a single lumen 25. In these and related embodiments, the bend 30*b* in members 30 can be achieved through use of a deflector 50, which deflects the electrode members as they are advanced out of the introducer. Typically, deflector 50 will be positioned in distal portion 25*dp* of lumen 25 but it can also be positioned in other locations as well. Deflector 50 comprises a series of individual channels 51 which direct electrode members 30 at a selected angle to achieve the amount of bend. Typically, the deflector will include at least three channels 51 with additional numbers also contemplated. The channels 51 may be radially equally distributed about the longitudinal axis 201 of the introducer (e.g., for three members they may be approximately 120° apart). Also, they may be formed in the body 52 of the deflector 50 and run along the length of the deflector from the proximal 53 to distal portions 54 of the deflector. The proximal end 55 of the deflector can be shaped to deflect electrode members 30 into the channels 51 as they are advanced through lumen 25. Also channels 51 may be sized so that only one electrode member 30 will fit into a channel. In use, these two features confer a self guiding capability to the deflector 50 so that the user can separately or collectively advance a desired number of electrode members 30 into the introducer and have them be guided into separate channels 51. In other embodiments, channels 51 can themselves be deflectable (e.g., through the use of piezo electric or other like materials, which can be deflected by electric current) so that the user can select and even modify the amount of bend in the deployed members 30. In use, such a feature would allow the user to change the amount of bend in members 30 while observing their position under fluoroscopic or other imaging modality so as to achieve and confirm a desired orientation of the electrode members. Such a feature would also allow the medical care giver to change the direction and orientation of members 30 so as to optimize or tune their detection capabilities to detect a foci F of ANEA in a particular area of the brain.

Figure 7A:
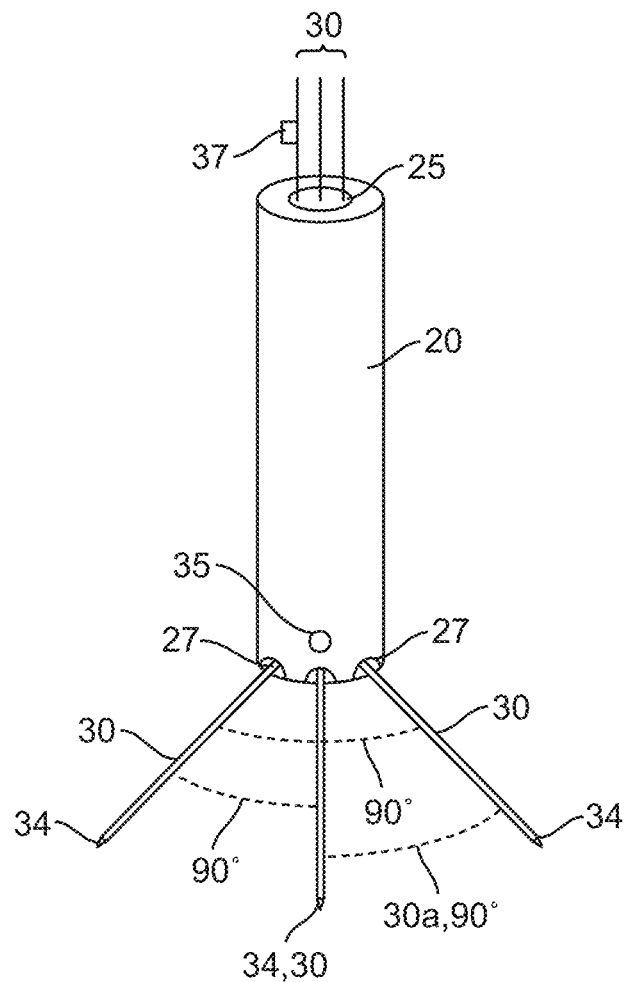
FIG. 7a is a perspective view showing an orthogonal orientation of the electrode members in the deployed state.
Figure 7B:
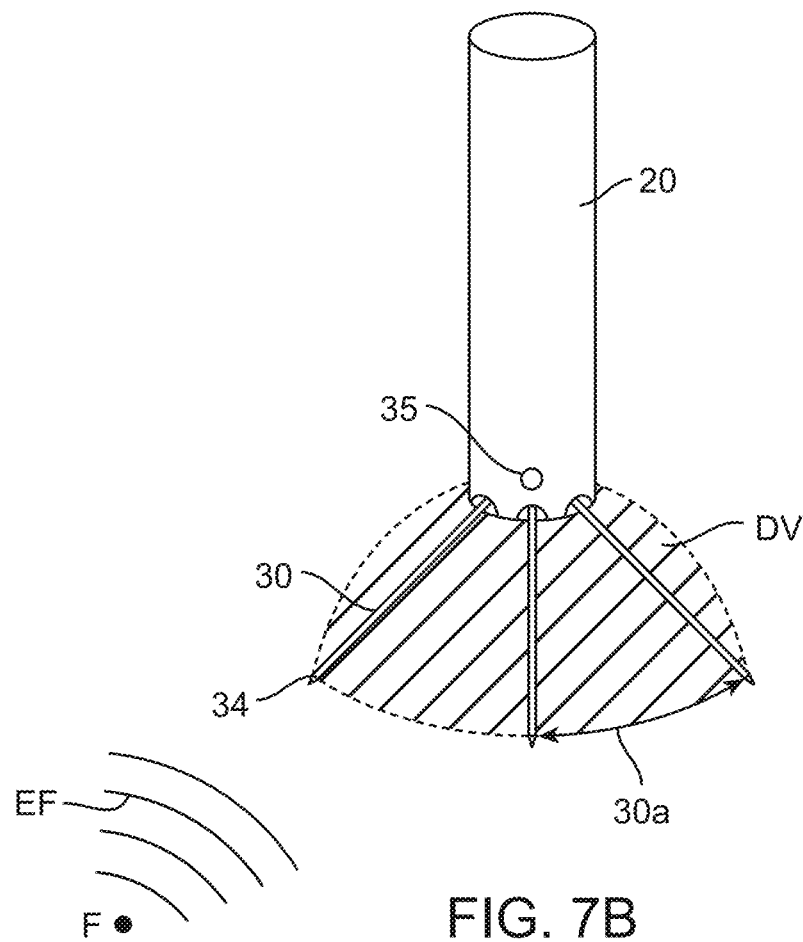
FIG. 7b is a perspective view showing the orientation of the electrode members and the detection volume defined by them in the deployed state.

Referring now to FIGS. 6a, 6b, 7a, 7b, 8a, and 8b, one or more embodiments provide that electrode members 30 have a non-deployed state when positioned in the introducer (as is shown in FIG. 6a) and a deployed state when advanced out of the introducer as shown in FIG. 6b. In the deployed state, the electrode members have an orientation which can detect a foci F of aberrant neural-electric activity. In one embodiment, this is achieved by configuring the electrode members to have a substantially orthogonal orientation with respect to each other. More specifically, with respect to the longitudinal axis 301 of each electrode member, the angle 30a between electrode members is approximately 90° so as to define a three dimensional Cartesian coordinate axis system, which corresponds to a detection volume DV as shown in the embodiments of FIGS. 7a and 7b. As will be discussed herein, this configuration allows the electrode members to measure voltages produced by an electric field EF generated by Foci F so as derive the electric field vector $\overline{E}$ including the direction and magnitude of the vector. For orthogonal orientations, the defined detection volume DV is substantially tetrahedral as shown in the embodiment of FIG. 7b. Other orientations defining other detection volumes DV are also contemplated such as various polyhedral shapes. For example, four electrode members can be configured to define a substantially pyramidal detection volume. Still additional numbers of electrode members such as six or more can be configured to define a detection volume which approaches a substantially conical shape.

Figure 8A:
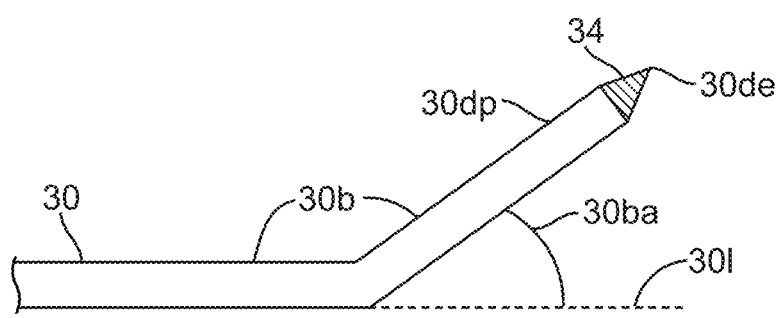
FIGS. 8a and 8b are side views illustrating embodiments of a bent electrode.
Figure 8B:
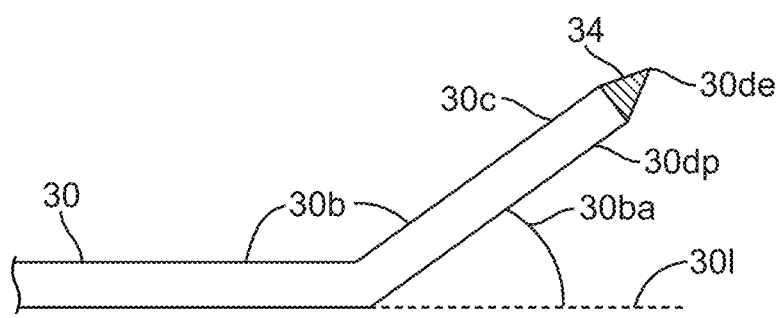

In the non-deployed state within the introducer, electrode members 30 are in a compacted state and substantially straight. As electrode members 30 are advanced out of distal end 22 they become distended so as to define a volume DV for detection of Foci F. The electrode members may include a bent shape 30b when advanced out of introducer 20. This can be accomplished by fabricating the electrode members to have spring memory to assume the bent shape 30b when advanced out of introducer 20. The bent shape 30b can also be accomplished by advancing the electrode members through bent lumens 25 or a deflector 50 as is described herein. The angle 30ba of the bend 30b can be in the range from 20 to 90°, with specific embodiments of 30, 40, 45, 50, 60, 70 and 80°. Bend 30b can be substantially abrupt as is shown in the embodiment of FIG. 8a or can have a selected amount of curvature to confer a curved shape 30c to the deployed portion 30dp of the electrode member as is shown in the embodiment of FIG. 8b.

Figure 9:
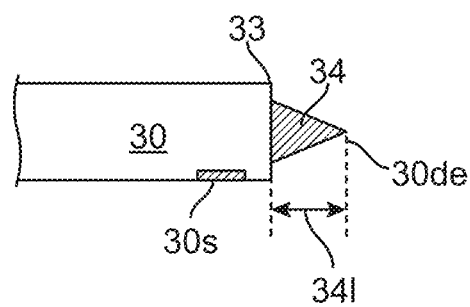
FIG. 9 is a side view illustrating an embodiment of the electrode member including an insulating sleeve and a conductive core.
Figures 10A, 10B:
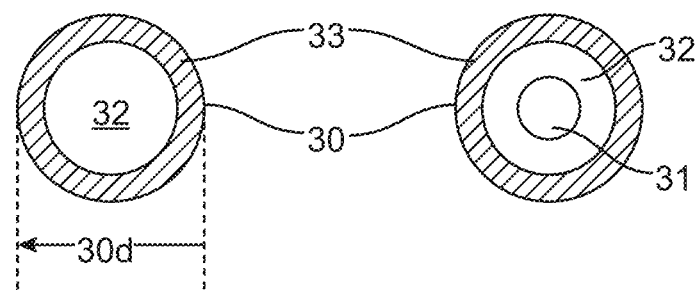
FIGS. 10a-10b are cross sectional views of embodiments of the electrode member.

Referring now to FIGS. 9, 10a, and 10b, typically, the electrode members 30 will comprise a conductive core 32 and an outer insulating sleeve or jacket 33 extending along most of the length of the electrode member so that the only tissue contacting conductive portion 34 of the electrode member is the distal end 30de. The length 341 of the conductive portion 34 will be 1 mm or less, though longer portions are also contemplated. In one or more embodiments, the length is in the range from about 0.75 to about 0.25 mm. The insulating sleeve 33 can comprise various insulating biocompatible polymers known in the art such as silicone and polyurethane. Sleeve 33 can also have lubricous properties to facilitate advancement of the electrode members into tissue. Also, sleeve 33 can contain various drug eluting compounds known in the art to reduce bio-adhesion to the sleeve (both cells and molecules). The conductive core 32 of the members 30 can be fabricated from various biocompatible conductive materials known in the art including metals and conductive polymers and like materials. An example of a suitable metal includes 304V steel. In some embodiments, members 30 comprise a shape memory material such as NITINOL. For particular shape memory embodiments, the advanced electrode members 30 can assume their deployed state as they are warmed by the brain tissue above the transition temperature of the selected shape memory material.

In many embodiments, the distal ends 30de of the electrode members have a pointed or other tissue penetrating shape to facilitate advancement into tissue. Also, electrode members 30 may sufficient stiffness to be advanced into tissue, but are sufficiently flexible to assume a curved shape when advanced out of the introducer. The stiffness and flexibility can be achieved by selection of the member diameter, material and material treatment (e.g., annealing) as is known in the medical guide-wire arts. In various embodiments, the diameter 30d of the electrode members can be in the range of 0.0005 to 0.018" with specific embodiments of 0.001, 0.005, 0.010 and 0.015". Typically, the electrode member 30 will be solid as is shown in the embodiment of FIG. 10a; however, in various embodiments, members 30 may have a lumen 31 as is shown in the embodiment of FIG. 10b. Lumen 31 can be used for intracranial delivery of one or more medications including both solid and liquid form medications. In such embodiments, members 30 can be fabricated from various hypotubes known in the art. Also in various embodiments members 30 may also include one or more sensors 30s for measuring various tissue properties which may be predictive of seizure or pre-seizure events. Accordingly, such sensors can include without limitation, pH, temperature, $pO_2$, $pCO_2$, glucose, and other biochemical related sensors. Measurements from such sensors can be combined with voltage/electric field vector measurements as means for determining pre-seizure and seizure events.

Figure 11:
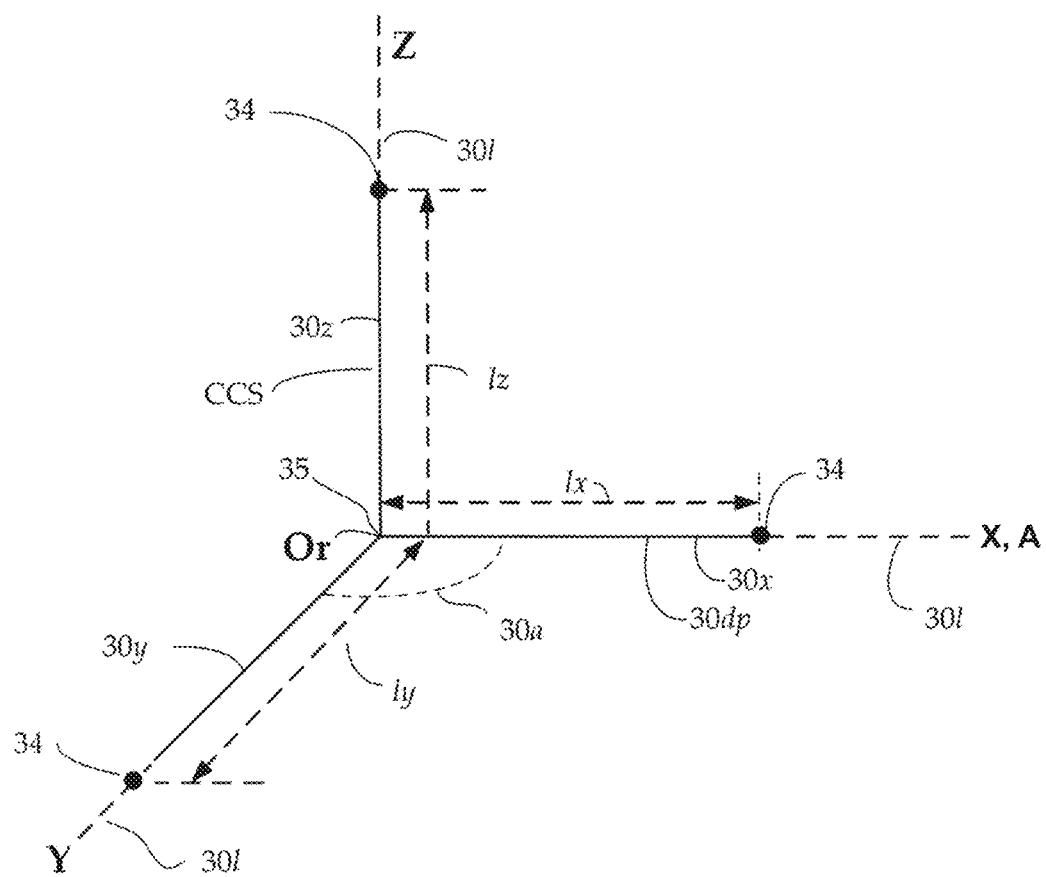
FIG. 11 is a graphical view illustrating alignment of the electrode members with a Cartesian coordinate system.
Figure 12:
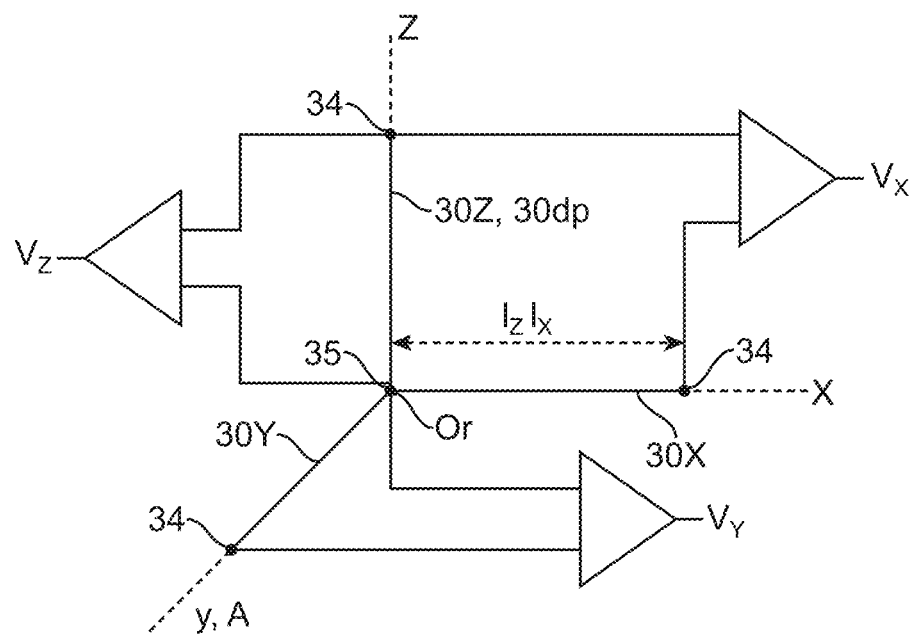
FIG. 12 is a combination graphical and schematic view illustrating alignment of the electrode members with a Cartesian coordinate system and generation of voltages the electrode members as a result of abnormal neural-electric activity.

Referring now to FIGS. 11-12, in many embodiments, the deployed portions 30dp of the electrode members 30 (i.e., that projecting out of the introducer 20) can have a substantially orthogonal orientation such that each electrode member 30 is oriented with an axis A of a Cartesian coordinate system CCS. The origin Or of the axes corresponds to the position of reference electrode 35 which typically will be at the distal end 22 (FIG. 6a) of introducer 20. This results in an x, y and z electrode member 30x, 30y and 30z. Each of these oriented electrode members project a selected distance 1 past reference electrode 35 resulting in distances $l_x$, $l_z$ and $l_z$ which in some embodiments are substantially the same. The electric field EF (FIG. 7b) generated by Foci F results in voltages $V_x$, $V_y$ and $V_z$ at respective electrode members 30x, 30y and 30z. The actual voltage being due to the potential difference between tissue contacting conductive portion 34 and reference electrode 35 which is typically positioned near introducer distal end 22). In many embodiments, electrode members 30x, 30y and 30z can share a common reference electrode 35 or each may have its own.

Figure 13:
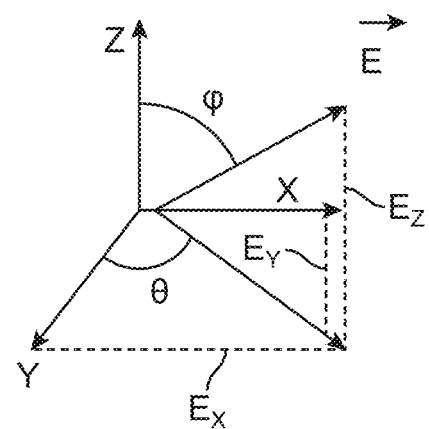
FIG. 13 is graphical view illustrating an electric field vector produced by aberrant neural-electric activity and its polar components.

A discussion will now be presented of the mathematical methods used to calculate the components of the electric field vector $\overline{E}$ generated by a foci F of abnormal neural-electric activity and the subsequent direction D of foci F relative to the distal end the introducer. These and other related methods along with equations 1-6 can be incorporated into algorithms 83 described herein. Referring now to FIGS. 11-13 and equations 1-6 below, electric field vector $\overline{E}$ has a magnitude E having scalar components $E_x$, $E_y$ and $E_z$ and angular directions θ and φ. Measurement of voltages $V_x$, $V_y$ and $V_z$ by electrode members 30x, 30y and 30z allows calculation of $E_x$, $E_y$ and $E_z$ using equation (1), the magnitude of the vector $\overline{E}$ can be calculated by equation (2). Equations 4-6 allow determination of the direction of vector $\overline{E}$ relative to origin Or (and hence the direction relative to introducer distal end 22) by virtue of determination of angles φ, and θ. Determination of this direction, then allows determination of the direction D of Foci F (relative to introducer distal end 22) from which vector $\overline{E}$ emanates.

$$E_x = V_x/l_x, \ E_y = V_y/l_y, \text{ and } E_z = V_z/l_z \quad (1)$$

$$|\overline{E}| = (E_x^2 + E_y^2 + E_z^2)^{1/2} \quad (2)$$

$$\cos \varphi = (E_z/|\overline{E}|) \quad (3)$$

$$\varphi = \cos^{-1}(E_z/|\overline{E}|) \quad (4)$$

$$|\overline{E}| * \sin \varphi * \cos \theta \quad (5)$$

$$\theta = \cos^{-1}(|\overline{E}| * \sin \varphi)/E_y \quad (6)$$

Figure 14:
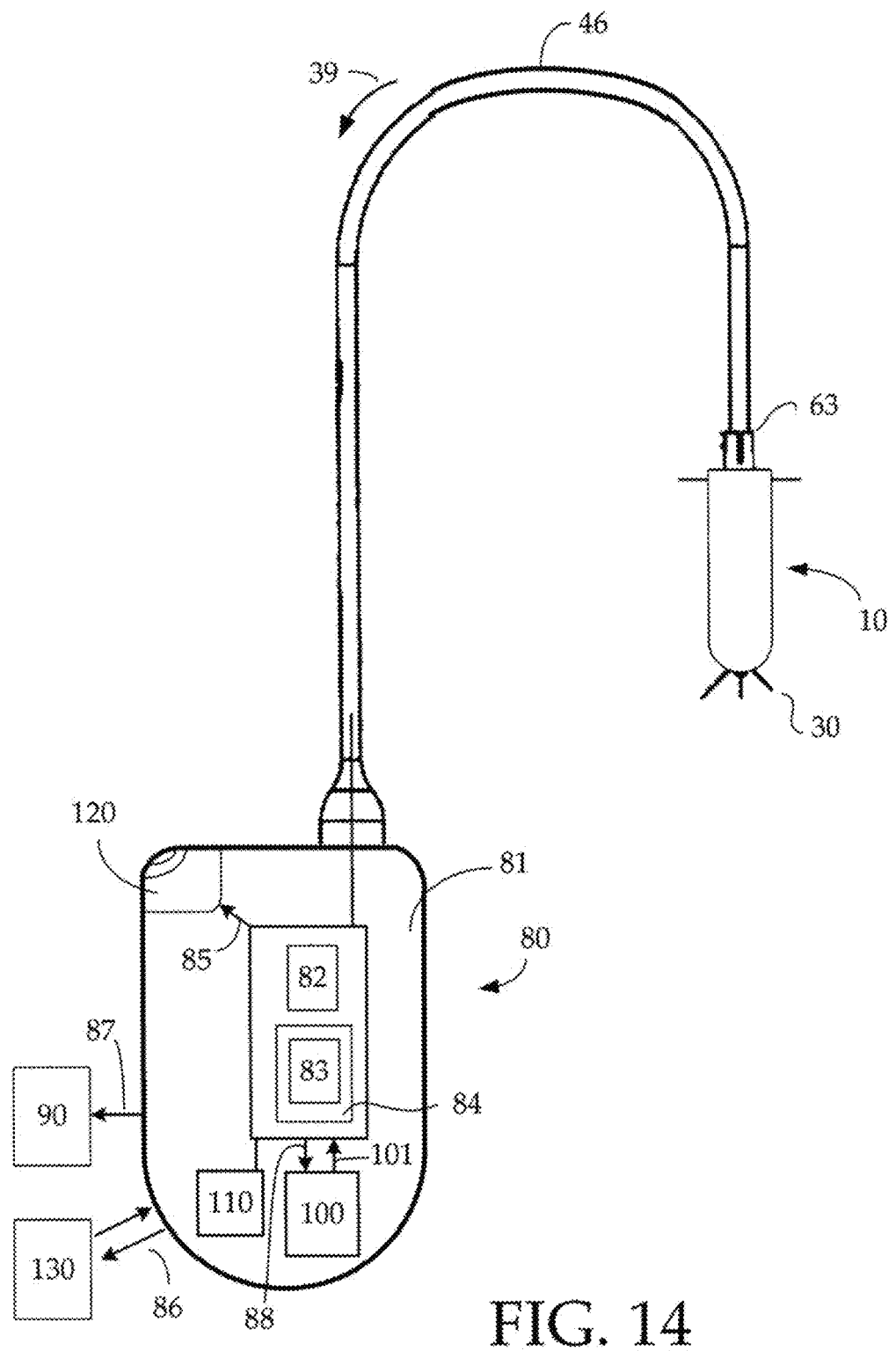
FIG. 14 is a block diagram showing an embodiment of a control module for use with various embodiments of the ANEA detection apparatus.
Figure 15:
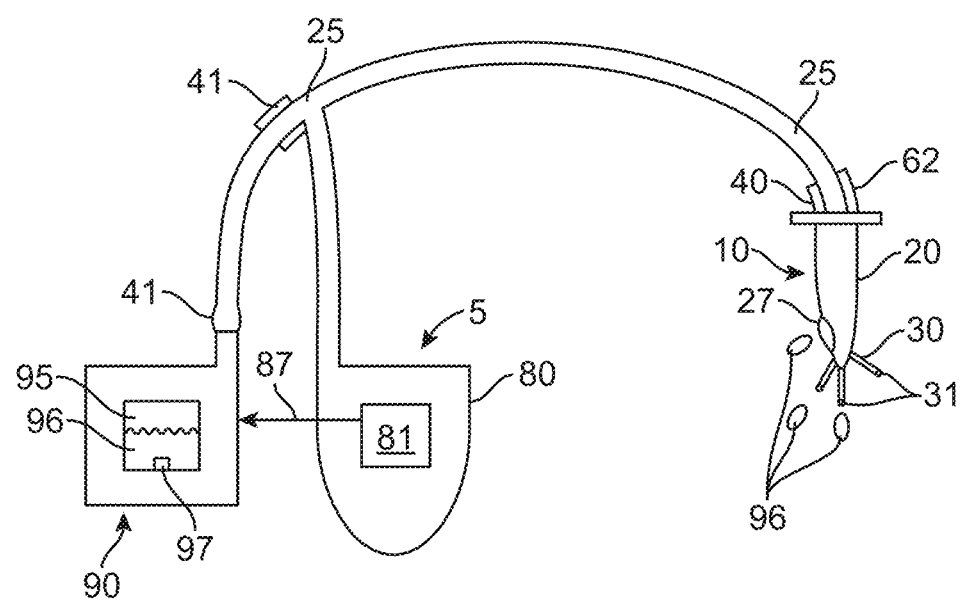
FIG. 15 is a block diagram/side view of an embodiment of the drug delivery device.
Figure 16A:
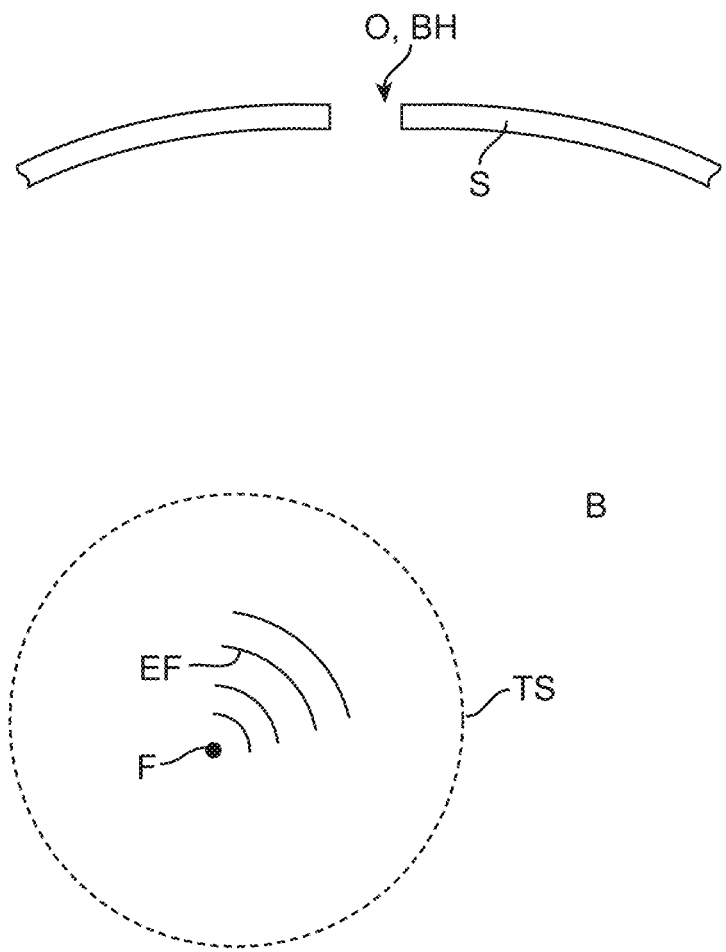
FIGS. 16a-16e are side views illustrating a method for introduction of the introducer and deployment of the electrode members to detect a Foci of aberrant neural-electric activity in a target tissue site in the brain.
Figure 16B:
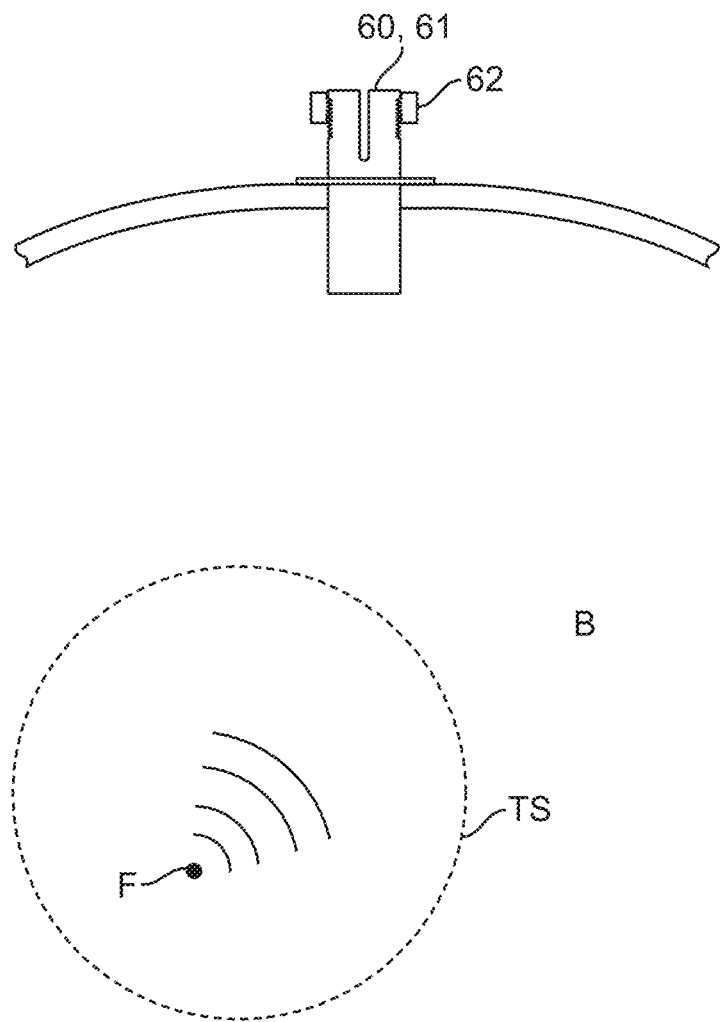
Figure 16C:
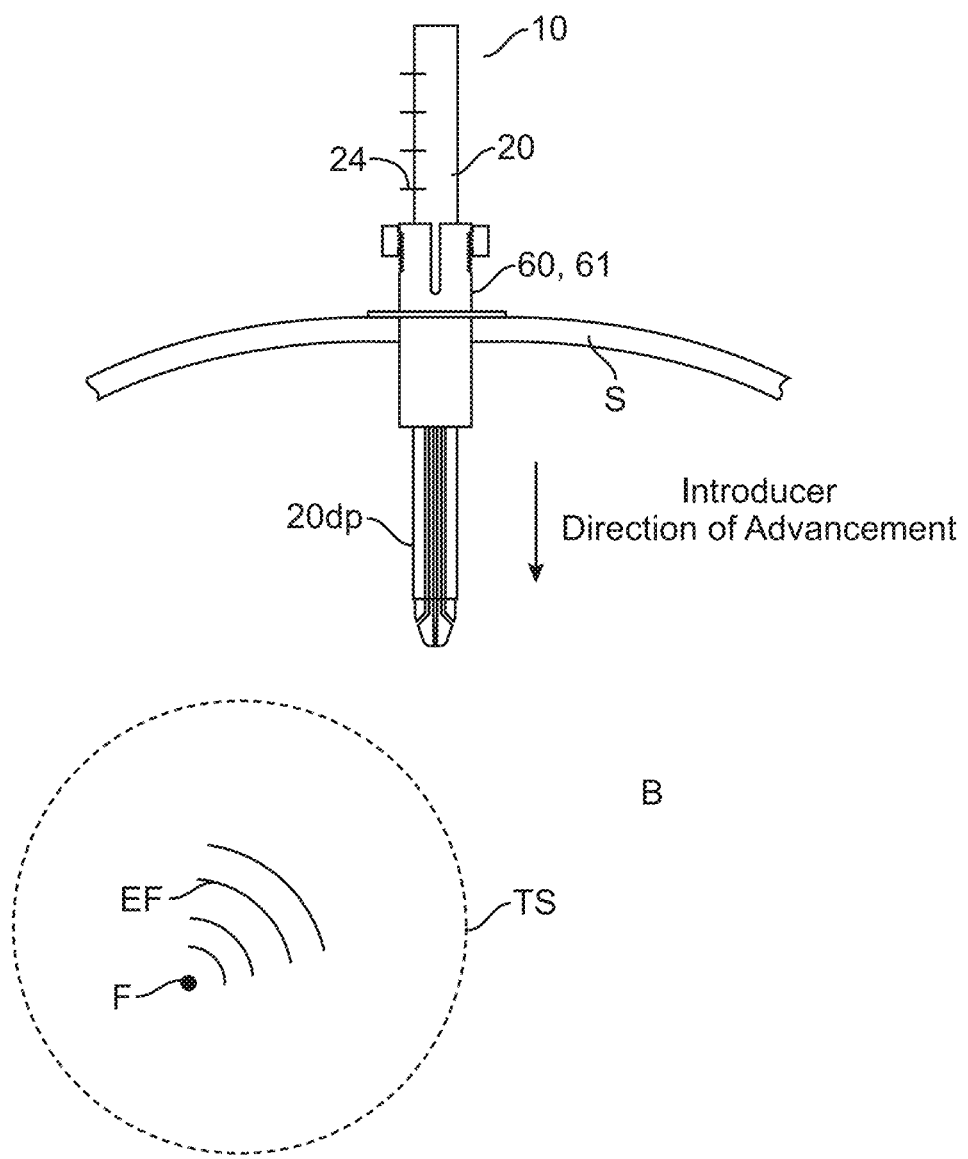
Figure 16D:
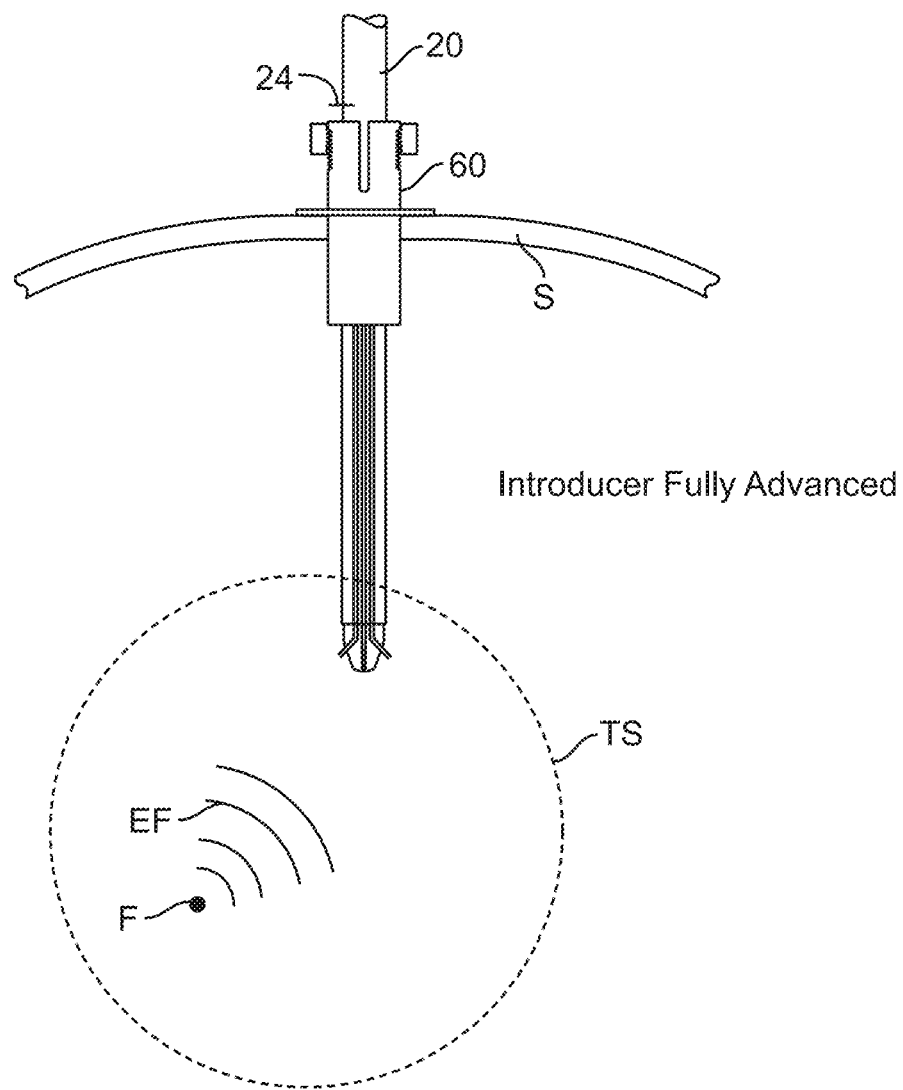
Figure 16E:
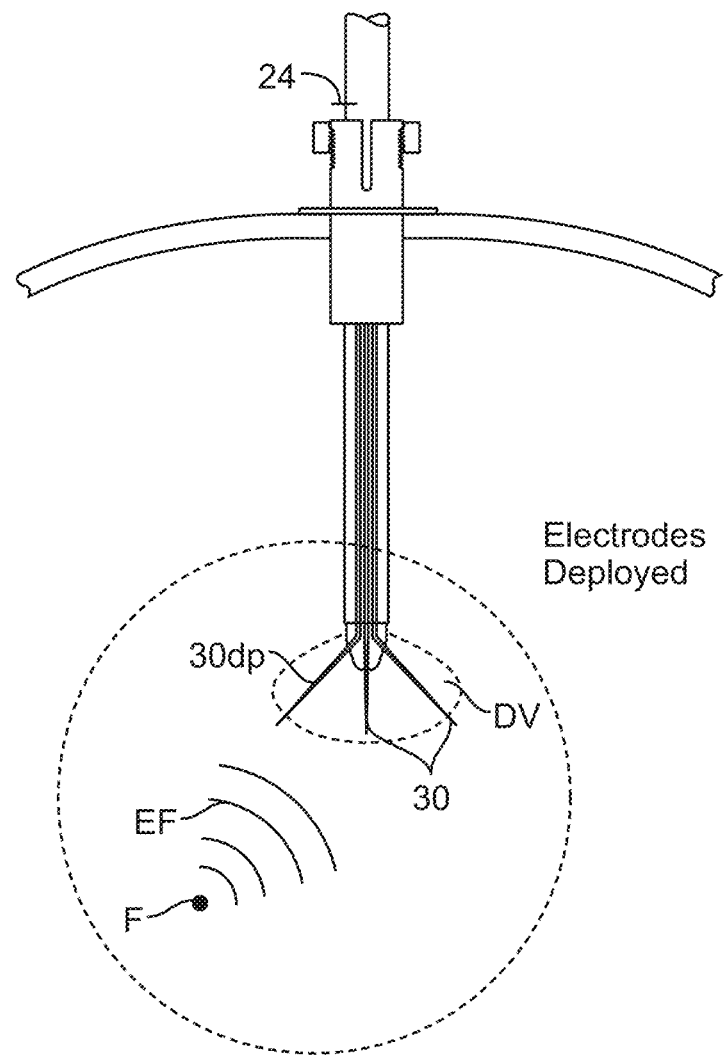

Referring now to FIG. 14-15, in many embodiments, apparatus 10 can be coupled to a control module 80 (see FIG. 1) (hereinafter module 80) that is configured to perform one or more functions. These can include storage and analysis of signals received from electrode members 30, sensors 63, detection of a pre-seizure or seizure event, alerting the patient and medical care provider of an impending seizure and control of various interventional actions to prevent a seizure including drug delivery and electrical stimulation of brain tissue. Module 80 can include one or more processors, state devices, circuits (e.g., power control, filters, etc.) alarms, batteries and other power storage devices. It can also include one or more communication resources 110 such as an RF communication chip for wirelessly communicating with external medical monitoring instrumentation using MICS or other medical wireless communication protocol. Module 80 may also be coupled to or include an integral drug delivery device 90 as well as brain stimulator 100 described herein. Control module 80 can be worn by the patient or may be configured to be implanted subcutaneously in the head and neck area (as shown in FIG. 2a) or other area in the body.

Module 80 will typically include at least one controller 81 which can comprise various logic resources 82 such as a processor, state device or a combination of both. Processor 82 can be off-the-shelf (e.g., such as those manufactured by Intel® or Texas Instruments®) or can comprise a custom chip such as an ASIC. Controller 81 may include one or more algorithms 83 which can be implemented through software, hardware or a combination of both. For software implementation, algorithms 83 can be stored in memory resources 84 (e.g., ROM, RAM, DRAM, etc) integral or coupled to logic resources 82. Algorithms 83 can be configured to perform a number of functions including without limitation: processing and storage of signals 39 received from electrode members 30; sensors 30s or 63, calculation of the components of an Electric Field vector $\overline{E}$ including the magnitude and direction D of the vector, detection of one or more of ANEA, a pre-seizure or seizure event; alerting the patient and medical care provider of an impending seizure and communicating with external medical monitoring instrumentation; and control of various interventional devices and actions to prevent a seizure such as drug delivery and electrical stimulation of brain tissue. As is described herein, various detection algorithms 83 can be configured to generate a detection score indicative of whether a pre-seizure or seizure event is occurring. Algorithms 83 can be configured to include one or more signal processing algorithms known in the art such as Fast Fourier Transforms, wavelet, fuzzy logic and like algorithms.

In many embodiments, module 80 includes a stimulator device or stimulator 100 configured to send an inhibitor signal 101 via electrode members 30 (or other implanted electrode) to prevent the onset of a seizure or stop an occurring seizure or otherwise reduce its duration. Stimulator 100 will typically comprise power control and charging circuitry and a discharging capacitor or other dischargeable power voltage source. It can also include various pacing and/or signal processing circuits to as to provide a duty cycle of inhibitory signals over an extended period of time.

Drug delivery device 90 can comprise one or more drug pumps known in the art including for example, displacement pumps (e.g., a piston pump), peristaltic pumps, screw pumps and like devices. It can be miniaturized for implantation in the head or neck area of the patient (e.g., at the base of the skull as shown in FIGS. 2a and 2c) or other portion of the body. Miniaturized pumps can comprise MEMs and/or bubble jet based miniature pumps. Also device 90 can be configured for one or both of intracranial or IV delivery. For intracranial delivery device 90, can be fluidically coupled to one or more lumens 25 of introducer 20 via connectors 40 and 41 so as to deliver the drug (either in liquid or solid form 0 through lumen 25 and/or through lumens 31 of hollow embodiments of electrode members 30. Connectors 40, 41 can include luer-lock, connectors, Touhy Borst adapters and other like devices. Delivery device 90 can also be configured for the delivery of liquids, solids or both. For liquid delivery, the device 90 can use one or more of displacement, rotary or peristaltic pumping devices. For solid delivery, a miniature screw pump can be used with other solid form delivery mechanisms contemplated. Typically, the device 90 will also include a reservoir 95 containing of one or more medicaments 96 (also referred to herein as medication 96) which may comprise solid, liquids, or both. Whatever the form, reservoir 95 may contain a plurality of doses of medication 96 sufficient for a prolonged time period. For embodiments where medicament 96 is in solid form, reservoir 95 may contain up to 500 or more doses of medication 96.

In other embodiments, reservoir 95 can also be separate from delivery device 90 though still coupled to it (e.g., fluidically or otherwise) via a catheter or like connecting member. In the later case, the reservoir 95 can be implanted subcutaneously or can even be positioned external to the body to allow for easier replenishment of drug (e.g., via injection through the skin). Delivery device 90 can also be configured to be controllable by signals 87 from module 80 and controller 81. Reservoir 95 can also include one more sensors 97 configured to sense the amount of drug (liquid or solid) remaining in the reservoir as to alert the patient or doctor when the reservoir needs to be replenished.

In one or more embodiments, the invention may provide a drug delivery system 105 shown in the embodiment of FIG. 2c for the intracranial delivery of one or more drugs to various regions within the brain (various components of system 105 which may correspond in or more aspects to system 5). Such drugs may include those for the treatment of one or more neurological conditions such as epilepsy, migraine headaches and depression. According to one or more embodiments, system 105 comprises a drug storage and delivery device 130 coupled to a drug delivery member 120 as is shown in the embodiments of FIGS. 2c and 2d. Delivery member 120 has a proximal end 121 coupled to device 130 and a distal end 122 positioned at or near a delivery site DS in the brain B, such as the ventricle V or other location. In various embodiments delivery member 120 may correspond to connector 45 and drug storage and delivery device 130 to device 90 and/or 80. As discussed further herein, storage and delivery device 130 is configured to be implanted subcutaneously, typically in the back or side of the patient's head or other location in or one the patient's body. Delivery member 120 can have sufficient length to extend from the back of the patient's head/skull or other implant location into the patient's brain to reach a delivery site DS including a site within a deep brain region of the brain. Further description of various drug delivery apparatus, systems and methods which may be used in one more embodiments of the invention may be found in U.S. patent application Ser. Nos. 13/645,344, 13/681,825 which are incorporated by reference herein in their respective entirety for all purposes.

The drug delivery member 120 will typically comprise a catheter 120 or other like flexible member having one or more lumens 123 which have an internal diameter sized for delivery of solid form drug 200 such as drug pellet 200 to a delivery site DS in the brain. All or a portion of catheter 120 can be configured to be subcutaneously implanted under the patient's scalp so that it can extend from device 130 to delivery site DS in the patient's brain. Accordingly, catheter 120 may comprise any number of biocompatible resilient polymers known in the art (e.g., silicone, PeBax, polyurethane, polyethylene (e.g., HDPE, LDPE), etc.) and may be formed using various extrusion methods also known in the art. Further the catheter may be sized (e.g., diameter) and otherwise configured (e.g., from resilient biocompatible materials) so that when implanted underneath the patient's scalp, it is minimally visible and/or does not impact hair growth or condition of the scalp. Further, the portions of catheter 120 which are implanted within the brain, including distal tip 120d are configured and otherwise structured to be atraumatic and unreactive with brain tissue. Such materials for the brain implanted portions of catheter 120 can include various silicones and polyurethane polymers. In one more embodiments, all or a portion of catheter 120 may be constructed from similar materials as those used in cerebralspinal shunts.

Device 130 includes a housing 131 having exterior surface 132 and interior space 133 (also referred to as interior 133). The housing also includes a port 135 for coupling to catheter 120. The housing may be fabricated from one or more biocompatible materials including one or more biocompatible polymers such as ABS, PE, PET; and metals such as titanium. Surface 132 may also be coated with or otherwise comprise one or more compatible materials including for example, silicone, polyurethane or PTFE. Housing 131 may be sized and shaped to be positioned in any number of locations in the head, neck or other area in or one the patient's body. In some embodiments, the housing is sized, shaped and otherwise configured to be implanted at the base of the patient's skull or nearby area.

Device 130 contains an engaging belt 140 having a plurality of doses 200d of medication 200 which are typically positioned within housing 131. Medication 200 comprises a drug other therapeutic agent 210 for treatment of a neurological condition and one or more excipients 220 as is described in further detail herein. Doses 200d may comprise solid and/or liquid-form medication elements 201. An example of the former can include a medication pellet and an example of the latter a liquid filled capsule. In some embodiments doses 200d comprise solid form medication elements 201 configured to dissolve in brain tissue and/or cerebrospinal fluid found bathing the brain. According to one or more embodiments store 140 corresponds to a belt 140 to which doses 200d may be attached. In such embodiments, device 130 may include a mechanism 150 (also referred to herein as transfer mechanism 150) for engaging belt 140 and transferring an individual dose 200d of medication 200 from the belt through port 135 to deliver it to a selected tissue delivery site DS and then advance the belt for the delivery of the next dose 200d of medication 200. In alternative embodiments, a separate mechanism/drive source (not shown) may be used for advancing belt 140.

According to many embodiments, mechanism 150 includes an advancement member 151 configured to advance medication element 201 from within the housing 131, through catheter 120 to delivery site DS. According to one or more embodiments, member 151 corresponds to a metal stylett which may comprise various shape memory metals (e.g., NITONOL, stainless steel) allowing the member 151 to be wound or otherwise contained in housing 131 in a non-linear shape and then be unwound to a linear shape. Member 151 may also be configured to bend and flex (and have other pushability characteristics known in the guide wire art) so as to be advanced through and negotiate the curves in catheter 120 in going from port 135 to the tissue site TS in the brain. Member 151 has may be driven by an electric motor (e.g., a linear induction motor) or other drive means known in the art electric. In particular embodiments, it may be driven by rollers 150r integral to otherwise driven by an electric motor Also, it may have a shaped distal tip 152 such as ball shape to advance element 201 through lumen 123. Doses 200d are typically individually packaged in packaging 141 (also referred to herein as packaging containers 141) which may integral with or otherwise attached to belt 140. Accordingly, in such embodiments mechanism 150 and member 151 may further be configured to puncture packaging container 141 and push out dose 200d. Various embodiments of the invention also contemplate other means for advancing medication element 201 through lumen 123 to delivery site DS. Such means may include, for example, pneumatic, hydraulic or magnetic drive means.

Packaging containers 141 may comprise various foil packaging known in the pharmaceutical arts and according to some embodiments are substantially impermeable to air and water vapor. In use such embodiments allow for the long term storage (e.g., years) of dose 200d in device 130. In some embodiments, multiple doses 200d (e.g., 2, 3, 4 or even more doses) of medication 200 may be packaged in an individual packaging container 141. Such doses may include the same or different drugs 210 allowing for the treatment of the same or multiple conditions. According to one more embodiments having multiple doses 200d in the same container 141, the container can include a first dose of drug 210 configured to rapidly dissolve in brain tissue to acutely treat an epileptic seizure or other neurologic condition (e.g., a migraine) and a second dose configured to more slowly dissolve so as to provide for a long maintenance dose to prevent the re-occurrence of the seizure or other condition.

In many embodiments, port 135 comprises a sealable septum 136 allowing a solid dose of medication 200 to be passed through the septum by mechanism 150 without the ingress of fluids into housing interior 133. Septum 136 can comprise various elastomeric polymers such as silicone or polyurethane which have sufficient resilience to open and then seal itself after being punctured or otherwise opened by the passage of medication element 201 such as a medication pellet.

As is described above, medication 200 typically comprises one or more drugs or other therapeutic agents 210 for the treatment of one or more conditions such as various neurological conditions described herein. Medication 200 may also include one or more pharmaceutical excipients 220 including for example, one or more of disintegrants, superdisintegrants, binders, anti-oxidants and other excipients known in the art. In some implementations, the one more excipients including are selected to be non-pyrogenic and otherwise inert with brain tissue. When in solid form medication elements may 201 correspond to tablets or pellets, with other shapes also contemplated (e.g., spheres). According to one more embodiments, when in solid form, medication elements 201 are configured to dissolve in brain tissue and/or in cerebral spinal fluid within the ventricles in brain to release drug 210. In some embodiments medication elements 201 are configured to rapidly dissolve in brain tissue and/or CSF so to acutely treat or prevent an epileptic seizure or other acute neurologic condition. In such embodiments, medication elements 201 may comprise various super disintengrants known in the art including super disintengrants which rapidly dissolve in CSF. Also in such embodiments, solid form medication element 201 may have a porous structure configured for rapid ingress of CSF into the interior space of the element. In particular embodiments the dose of the selected drug 210 (e.g., furosemide or other loop diuretic) can be titrated based on a measurement of the volume of all or a portion of the patient brain. Such measurement may be made by MRI other medical imaging method known in the art. The particular volumes measured can include the total volume of the brain as well as the volume of space in the ventricles. The later measurement providing an indication of the volume of CSF within the brain which in turn allows for the achievement of a selected concentration of drug in the CSF. In use, such embodiment allow for delivery of a dosage of drug to the patient to more precisely achieve obtain a desired therapeutic index for a given drug. This in turn, results in a more efficacious clinical effect (e.g., blocking of ion pump co-transporters causing cortical spreading depression) while minimizing adverse side effects (e.g., adverse peripheral effects such as electrolyte loss, excess diuresis, etc.).

Referring now to FIGS. 2*b* and 16*a*-*e*, a method of introducing introducer 20 and deploying electrode members 30 will now be discussed. Prior to introduction of apparatus 10, a patient having epilepsy or other condition characterized by ANEA can undergo a series of EEGs or other related brain scans to determine the location and other characteristics of a foci of ANBNEA likely causing the condition to be treated (similar method may also be used for determining origins of cortical spreading depression). This information can then be used to determine the target tissue site TS for deployment of the electrode members and thus the corresponding site in the skull for the introduction of the introducer. In many cases, the introducer can be introduced through a burr hole plug; however, it will be appreciated this is exemplary and that other approaches are equally applicable. After the burr hole BH has been drilled and burr hole plug 61 is positioned, the introducer is advanced into brain tissue to the target tissue site TS. The advancement can be done under fluoroscopic or other form of medical imaging observation. Positioning of the distal tip 22 of the introducer at the target site TS can be facilitated by the use of a distal tip marker on the introducer. Additionally, the introducer can include graduation markings 24 along its length indicating the depth of insertion. Once inserted to the desired depth, the surgeon can then lock the introducer in place using locking device 62. Determination that the introducer has been locked in place can be achieved through a signal sent by, for example, contact sensor 63.

Electrode members 30 can then be deployed to achieve a detection volume DV having a selectable size and shape. The electrode members 30 can be deployed individually, or collectively. They can also be advanced by hand or using an advancement member 28 (coupled to the proximal portions of the members 30) or by other advancement means known in the art. The depth of insertion of the electrode members can be controlled by, for example, using a stop placed on advancement member 30 (not shown) and/or by means of a stop 37 (FIG. 3) placed on each electrode member 30. Deployment of members 30 can also be guided by fluoroscopic observation or other imaging modality. In some embodiments, this process can be facilitated by superimposing onto the fluoroscopic image (or other image) a marker or other indicia denoting the likely location of the foci F of ANEA. This physician can use this marker to locate and orient the position of the deployed electrode members so as to optimize the detection of ANEA signals from Foci F. For example, the physician can use the marker to deploy the electrode members such that their distal ends are placed within a selectable distance of Foci F. Also, it can be used to achieve a selectable angular orientation, e.g., 90°, with the longitudinal axis of one or more of the electrode members so as to maximize the voltage produced at those electrode members from an electric field vector generated by ANEA signals from foci F.

After deployment of the electrode members, the physician can perform one or more tests to ascertain that the electrode members are functioning and capable of detecting ANEA signals from one or more foci F. This can include sending a test signal from a separate electrode (not shown) positioned in the brain so as to have the same directional orientation with respect to the electrode members as Foci F does. The test signal can be configured to simulate the amplitude and frequency of an actual ANEA signal. If the electrode members are not able to detect the test signal, the physician can redeploy all or a portion of the electrode members until the person gets the desired response. In particular embodiments, the test signal can not only be used to test the functionality of the deployed electrode members, but also as a beacon to assist in their deployment. In such embodiments, the physician can deploy and position the electrode members while the test/beacon signal is being sent so as to maximize the resulting voltages measured by the electrode members. After the electrode members 30 are correctly deployed, the electrode members can be locked in place using locking device 63 or another locking mechanism. The burr plug will then be sealed/closed using standard methods known in the art and connectors 40 (FIG. 6*a*) can be connected to control module 80 (or other like device) via one more wires or the connection can be wirelessly. The control module 80 can be implanted subcutaneously in the head and neck area or can be worn by the patient. In embodiments where module 80 contains a drug delivery device 90 for treating the foci F of ANEA, the module 80 will typically be implanted subcutaneously in the head and neck area. In embodiments where it does not, it can positioned in any number of location or can be worn by the patients. In such embodiments, a separate drug reservoir and drug delivery device (which may be substantially the same or different as device 90) can be implanted in the head and neck so as to provide for intracranial delivery of the drug. Alternatively, the drug can be delivered intravenously (IV) in which case the reservoir and drug delivery device can be positioned at any number of locations and/or externally worn by the patient. In embodiments where a combination of intracranial and IV delivery are used, a drug reservoir/delivery device can be implanted in the head and neck areas and another delivery device/reservoir can be worn by the patient for IV delivery.

Figure 17A:
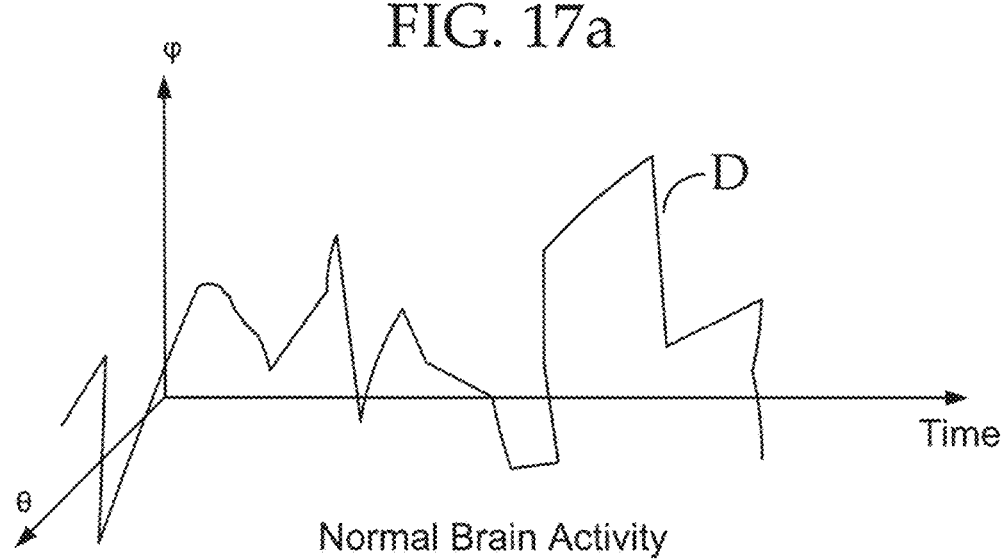
FIGS. 17a and 17b are 3d plots of the direction of an electric field vector over time in the brain.
Figure 17B:
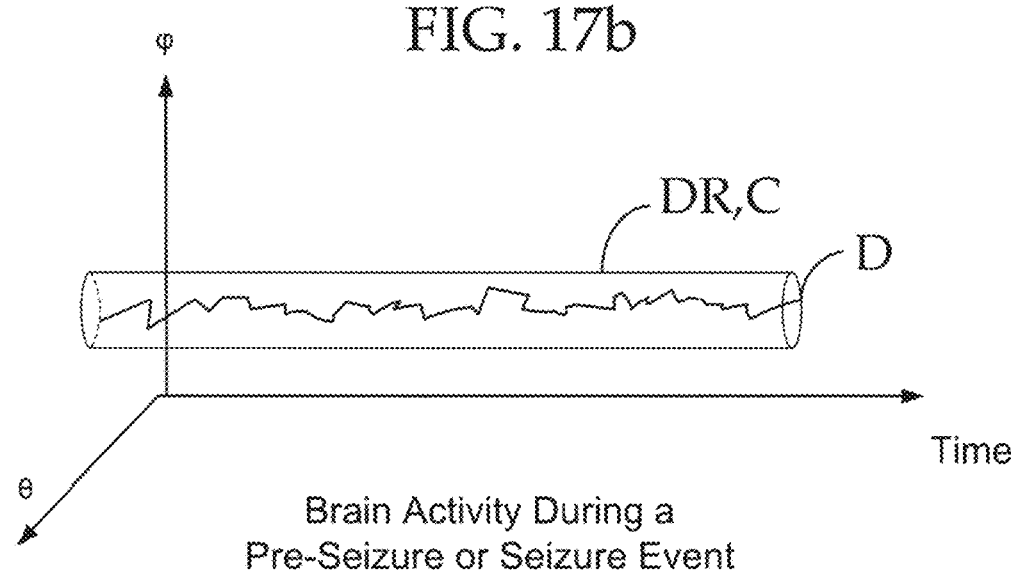
Figure 18:
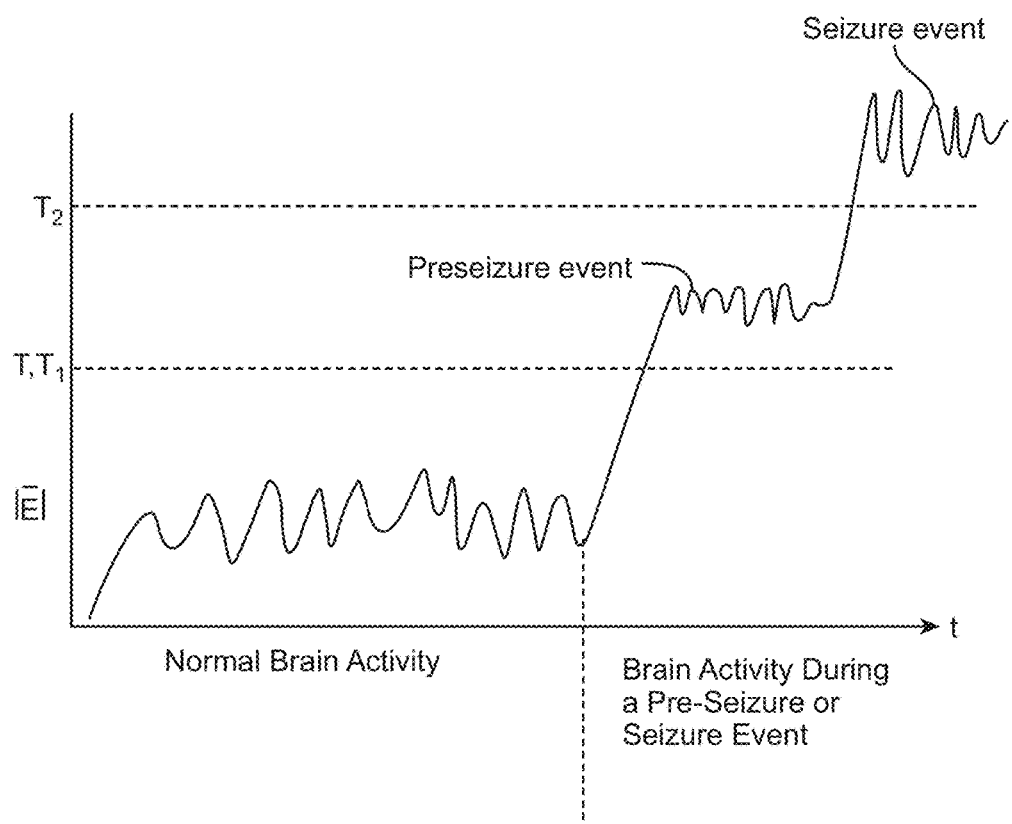
FIG. 18 is plot of the amplitude of an electric field vector over time during periods of normal and aberrant neural-electric activity in the brain.

A discussion will be presented of methods of detecting ANEA using apparatus 10 and utilizing this information, to detect a neurological event or condition such as a seizure. In these and related embodiments, methods will be presented for detecting both a pre-seizure event and a seizure event (such events can correspond to pre-seizure and seizure states). For ease of discussion, the pre-seizure and seizure events will refer to an epileptic pre-seizure event (also as a pre-ictal state or event) and epileptic seizure event (hereinafter seizure); however, it will be appreciated that these methods are applicable to detecting pre-seizures events/ states and seizures associated with other neurological events or conditions and syndromes such as migraine headaches and other related conditions. As discussed above, apparatus 10 measures electric field vectors in the brain generated by neural activity by measuring the voltage differential between each electrode member 30 and the reference electrode 35 and using these values to calculate electric field vector $\overline{E}$. Various characteristics of field vector $\overline{E}$ can then be used as an indicator of a seizure or pre-seizure event. Referring now to FIGS. 17-18, during normal brain activity, the electric field vector $\overline{E}$ will typically have a random direction D (as defined by angles $\varphi$ and $\theta$ described above) as is shown in FIG. 17a. Also during normal activity, the magnitude/amplitude $|\overline{E}|$ of the electric field vector will be random but will have a time average value which stays below a particular threshold T as is shown in FIG. 18. In contrast, during a period of aberrant neural-electric activity such as that occurring during a pre-ictal event or a seizure event, electric field vector $|\overline{E}|$ will dwell in a particular direction D or directional region DR for an extended period of time compared to normal brain activity as is shown in FIG. 17b. The dwell time can be tenths of a second to several seconds or longer (e.g., 0.10 to 10 seconds with specific embodiments of 0.2, 0.5, 1, 2, and 5 seconds) shorter dwell times are also contemplated (e.g., 0.01 to 0.1 seconds). During a preseizure or seizure event, the directional region DR will be bounded by a cylinder C or related geometric shape. Also, the electric field amplitude will exceed a threshold T above normal activity for a sustained period of time as is shown in FIG. 18. This can include exceeding a first threshold $T_1$, for a pre-seizure or other like event and a second threshold $T_2$, for a seizure or other like event.

In particular embodiments, algorithms 83 resident within module 80 can use one or more of the above changes in electric field vector characteristics (e.g., in amplitude and direction of the field vector) to detect a period of ANEA indicative of a pre-ictal event, epileptic seizure, a wave of cortical spreading other seizure or neurologic event, or such periods of ANEA can thus be used as a marker of a pre-ictal event, epileptic seizure cortical spreading depression or other seizure or neurologic event. For example, a pre-ictal event or seizure may be detected based on the electric field vector staying in a particular direction or directional cone for longer than a selected period of time. For applications where the location of a known foci of ANEA has previously been determined prior to placement of apparatus 10, additional algorithmic weightings can be employed if the direction of the detected electric field vector is within a selected directional cone that includes the direction of the previously detected Foci F (this direction being the direction of the foci relative to distal end of the introducer).

In another example of a predictive electric field vector characteristic, a pre-ictal event or seizure may also be detected based on whether the electric field amplitude exceeds a particular threshold and more specifically, whether the time average of the electric field amplitude exceeds the threshold. A combination of these two approaches can also be used so that the direction and amplitude of the electric field vector both need to exceed threshold values. Additionally, pattern recognition algorithms can be employed to detect particular signal patterns in the electric field which are indicative of a pre-ictal event or seizure (also known as a seizure event). A data base of such patterns can be generated from EEG measurements taken from the patient themselves, an epileptic patient population or a combination of both. Again, the detection algorithm can employ both pattern detection with one or both of electric field amplitude and direction so to make a determination of pre-ictal event or seizure. A detection score exceeding a certain threshold can be used to predict a pre-ictal event or seizure, with a score over a first value indicative of value pre-ictal event and a score over a second value indicative of a seizure. Also, weightings can be assigned to these or other detection parameters so that algorithm generates a detection score value as a function of these parameters. Weightings can be chosen from a weighting database taken from a patient population or they can be established for each individual patient by monitoring the patient over a period of time using external EEG electrodes or with apparatus 10 in place and then inducing a pre-seizure or mild epileptic seizure and recording the data for the these detection parameters. The weightings can also be updated after subsequent pre-ictal events or seizure either manually by a health care provider or by algorithm itself using self learning methodology.

When the detection score exceeds a threshold value indicative of a pre-ictal event or seizure event, module 80 can perform one or more functions. First, now referring to FIG. 14, the module can send a signal 85 to an alarm 120 to alert the patient so that they can take precautionary measures such as taking medication as well as sitting or lying down or discontinuing any hazardous activities. It can also send a wireless signal 86 (via a RF or IR port to a monitoring device 130 in a hospital or doctor's office (this can be achieved using a cellular phone or various medical telemetry devices known in the art). It can also send a signal 87 to a drug delivery device 90 to deliver a dose of an anti-seizure medication (e.g., a solid dose of a loop diuretic such as furosemide) and/or a signal 88 to a stimulating device 100 to send an inhibitor signal 101 via electrode members 30 (or other implanted electrode) to prevent the onset of a seizure or stop an occurring seizure. In various embodiments a combination of both interventions can be used. Inhibitory signal 101 can have various forms. In one embodiment, it can be configured to depolarize the regions of the around the Foci F causing the pre-ictal event or seizure. In other embodiments, it can be matched to the particular pattern of aberrant neural-electric activity causing the pre-ictal event or seizure so as to be out of phase with the aberrant neural-electric activity or otherwise dampen its effect on surrounding tissue. In some embodiments, the inhibitory signal is delivered using electrode members 30 as stimulating electrodes 36; however, the use of separate electrodes as stimulating electrodes is also contemplated.

For embodiments employing drug intervention, the delivered dose of drug can be titrated based upon the value of the detection score and/or whether the detected event is a pre-ictal event or a seizure. A baseline dosage can be determined based upon various patient parameters, such as weight, age, type of epilepsy (e.g., partial-onset seizure) and severity of seizures. Suitable anti-seizure medications can include phenytoin sodium (Dilantin), ion transporter agonists such as thiazides and thiazide-like diuretics, cation chloride ion transport agonists such as furosemide, and furosemide like diuretics as well as the chemical analogues and derivatives of each. In some embodiments, the anti-seizure compound corresponds to furosemide including its solid form. Still other anti-seizure medications known in the art also contemplated. During and after drug delivery, system 10 can be configured to continue to monitor brain activity to determine if the pre-ictal event or seizure has subsided and to what degree. Repeat dosages of drug can be administered as needed depending upon the detection score or other factor. Increased dosages can be given if the detection score remains above a selected level. Also, selectable dosing regimens can be used depending upon one or more of the detection score, type of epilepsy, pattern of seizures, age, weight, etc. For example, for a pre-ictal event, a bolus dose could be given intracranially (e.g., a dose of furosemide or other loop diuretic and/or ion co-transporter antagonist), whereas for a full seizure, treatment could include an intracranial bolus or initial dose (e.g., a loop diuretic, and/or ion-transporter antagonist) followed by a second dose which may be administered over a longer term than the first dose (e.g., a period of minutes or hours). The second dose may be the same or a different drug and may be administered intra-cranially or by another administration route such as intravenous. For embodiments where the same drug is used for both doses, the second or maintenance dose may be the same or set percentage of the first does, for example, 50, 25 or 10% by weight (or other parameter) of the first dose. Also in various embodiments, a selectable dosing regimen can be delivered based not only on an individual detection score, but also based on a time pattern of detection scores, even if the scores are below a pre-ictal event or seizure event threshold. For example, a dose of drug could be delivered based upon a certain number of spikes in the detection score over a selected period of time. Various dosing regimens can also be configured to use a combination of intracranial and IV administration using an intracranial delivery device and an IV pump.

In various embodiments, the dosing regimen can be tailored to the particular drug or combination of drugs delivered. For use of furosemide or other like drug, the dosing regimen can be in the form of an initial or bolus dose configured to achieve a selected peak intracranial concentration and/or therapeutic effect (e.g., prevention or slowing of cortical spreading depression) with a subsequent maintenance dose or doses of the same or a different drug to prevent the re-occurrence of cortical wave depression. In particular embodiments including use of multiple seizure drugs, the detection score can also be used to determine what drugs are actually given. For example, a detection score above a first threshold can be used for a first drug and another detection score above a second threshold can be used to select a second drug.

in various other embodiments of methods for detecting aberrant neural-electric activity causing a seizure or pre-seizure event (and/or cortical spreading depression associated with it), changes in tissue impedance can also be used with such changes being measured by electrode members 30. Such approaches operate on the principle that the impedance of brain tissue changes during a pre-seizure or seizure state. Tissue impedance can be measured by applying a slight voltage or current between conductive portion 34 (FIG. 6b) and reference electrode 35. Both real and the imaginary component of impedances can be used. Similar to methods employing voltage/electric field vector measurements, measured impedances can be used to generate detection score as mean do predict both pre-seizure and seizures events. In particular embodiments, impedance measurements can be combined with voltage/electric field vector measurements to further improve the sensitivity for predicting both pre-seizure and seizures events.

Cortical Spreading Depression: Cortical Spreading depression (CSD) is a propagating wave of transient neuronal hyper excitability followed by a period of electrical silence. This wave of excitation-inhibition moves slowly (~3-5 mm/min) across cortical and other areas of the brain. CSD involves a massive redistribution of ions (e.g., $K^+$, $Na^+$, $Ca2^+$, $Cl^-$) between intracellular and extracellular compartments. Glial cells are intimately involved in these ionic fluxes. Therefore, ion pumps (specifically Na+-K+-2Cl— (also described as NKCC1) co-transporters) on glial cells are implicated in CSD. These pumps utilize ion-dependent transporters. Accordingly, various embodiments of the invention contemplate use of ion-dependent transporters agonist (e.g., furosemide or other loop diuretic) to block or slow the ion fluxes responsible for cortical spreading depression associated with a neurological epileptic pre-seizure or other adverse neurological event or condition such as migraine headaches.

Treatment of Cortical Spreading Depression and Epilepsy Using Furosemide: Furosemide I (available under the trade name LASIX) is a well established loop diuretic used to treat fluid retention and high blood pressure. Loop diuretics are a class of drugs which act on the ascending loop of Henle in the kidney. Specifically they block a co-transporter (known as The Na—K—Cl co-transporter or NKCC, SLC12A2) resulting in reduced reabsorption of NaCl and Potassium in the nephron, in turn resulting in increased diuresis i.e., urine production. They are primarily used in medicine to treat hypertension and edema. Furosemide both in epileptic animal models and in human patients has been shown to block evoked and spontaneous epileptic neural activity and subsequent cortical spreading depression by blocking a similar ion-transporter in the brain. However, furosemide has a number of adverse side effects including, for example, electrolyte loss/imbalance, hyperglycemia, otoxicity, hyperuricemia and resulting gout, and low potassium levels as well as increased diuresis to name a few. If the drug were to be given orally and/or intravenously in concentrations sufficient for the prevention of epilepsy one or more of these side effects would occur, precluding its use and/or significantly limiting its applications. Patients would also have to be regularly monitored for one or more of these conditions including electrolyte loss (e.g., loss of electrolytes such as Na, K, Cl, Ca. Mg, etc.). Further, for acute situations (e.g., the onset of a seizure), oral administration would not be fast enough as the drug may take 30 minutes or longer to get into the patient's blood stream—if they were even able to take the drug at the onset of the seizure due to the loss of motor control which occurs at the onset of the seizure. IV administration would also be impractical since patients may not be able to inject themselves fast enough after the seizure began (even if they carried around an syringe of the solution), particularly since they quickly loose motor control at the onset of the seizure.

Various embodiments of the invention overcome these problems by providing apparatus, systems and methods for the treatment and prevention of epilepsy (and other conditions associated with CSD such as migraine headaches) by the use of intracranial delivery of furosemide (and/or its analogues and derivatives) so that the drug is delivered directly to the patient's brain. Further because the drug is delivered directly to the brain, the dose used to treat and/or prevent the epileptic seizure can be substantially less than would cause any appreciable undesirable peripheral effects, such as increased diuresis, electrolyte loss, hyperglycemia, etc., as is explained in further detail herein. In many embodiments, the delivery of furosemide and/or its analogues and derivatives is done intra-cranially using for example various embodiments of a drug delivery apparatus described herein. This apparatus may comprise a drug storage chamber coupled to an intracranial catheter that is inserted and positioned into the patient's brain tissue (including for example, deep brain tissue) through a burr hole or other opening made in the patient's brain tissue with an adaptive fitting positioned in the burr hole allowing for the long term placement of the catheter in the brain. In some embodiments, the apparatus can be configured for the delivery of a solid medication into the brain, so as reduce the risk of any pathogens (which are more likely to be present in liquid form) while allowing for the long-term storage of a multi-year supply of doses of furosemide in the storage chamber which may be subcutaneously implanted at the base of the skull for rapid advancement of the solid drug into the brain. In addition to the delivery of furosemide for the treatment of epilepsy or other condition associated with CSD, various embodiments of the invention also contemplate other loop diuretics, for the treatment of CSD associated conditions including for example, bumetanide, ethacrynic acid and torsemide.

In various embodiments, the dosage of furosemide (or other loop diuretic) is selected to produce a localized effect in the brain for seizure prevention, while minimizing peripheral effects, in particular effects on the kidneys causing diuresis and electrolyte loss. The dosages of furosemide (and related analogues and derivative) may be at least ten fold below the threshold dosage which produces a significant increase in diuresis and/or significant decrease in the patient's electrolyte level(s) (e.g., sodium, potassium). As used herein, a significant increase in diuresis is more than about a 10% increase in the patient's urine production (more specifically more than about a 5% increase), which may correspond to either a rate of urine production or total output over a period of time (e.g., one hour, two hours, 12 hours, etc.). Also, as used herein, a significant decrease in an electrolyte is more than about a 5% decrease a patient's plasma concentration of an electrolyte, for example, potassium or sodium concentration. Still smaller decreases are also contemplated such as decrease of more than about 2.5% or even 1%. Also, decreases of other electrolytes are also contemplated as well, for example, calcium, magnesium, hydrogen phosphate and hydrogen carbonate. Also, decreases in the patient's electrolyte level in other areas and/or tissues of the body are contemplated, such as decrease in their electrolyte level(s) in their interstitial fluid, intracellular fluid, muscle tissue, heart tissue, pancreatic tissue and other areas as well.

The aforementioned threshold dose(s) of furosemide for many patients is approximately, 20 mg. However, that threshold may be adjusted based on or more of a patient's, weight, age and medical condition (e.g., epilepsy, type of epileptic seizure, frequency of seizures, etc.). Various dose response curves and urine output measurement methods may be used to determine the specific threshold dose in a given patient, patient population (e.g., women with epileptic seizures) or subpopulation (women between 40-50 with grand mal seizures). Thresholds may also be determined using correlations to thresholds determined by such methods in one or more animal models (e.g., a rat, monkey, pig, etc.). Accordingly, in various embodiments, the therapeutically effective dosage of furosemide (and/or its analogues and derivatives) delivered to the brain of the patient can be in the range of can be in the range of about 1 to 2000 µg, about 200-800 µg, about 1 to 1000 µg, about 1 to 10 µg, about 5 to 50 µg, about 10 to 100 µg, about 10 to 500 µg, about 10 to 250 µg, about 20 to 250 µg, about 10 to 100 µg, about 25 to 100 µg, with still other ranges contemplated. In particular embodiments, the dosage of furosemide or other loop diuretic can be titrated based upon a measurement of the ventricle volume in the patient's brain (e.g., by MRI) so as to produce a selected concentration of drug in the CSF fluid in that volume. Further in various embodiments, one or more of the previous dosages of furosemide (and/or its analogues and derivatives) can be delivered intra-cranially, using for example, one or more embodiments of drug delivery systems and apparatus described herein such for example a system 105 and drug delivery device 95 and/or 115.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, various embodiments can be sized or otherwise adapted for various pediatric applications or the treatment of any number of neurological events or conditions involving aberrant neural-electric activity and/or cortical spreading depression.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand-alone elements. Hence, the scope of the present invention is not limited to the specifics of the described embodiments, but is instead limited solely by the appended claims.

What is claimed is:

1. A method for preventing or treating an epileptic seizure in a patient, the method comprising:
    detecting an epileptic pre-seizure event or seizure event in the patient's brain, wherein detecting an epileptic pre-seizure or seizure includes generating a detection score;
    storing doses of a loop diuretic compound in a subcutaneously implanted storage device, the storage device comprising a belt within the storage device to which the doses are attached; and
    delivering intra-cranially to the patient's brain, a dose of the loop diuretic compound from the belt to prevent or reduce a duration of the epileptic seizure, wherein the delivered dose of the loop diuretic compound is below a threshold, based on a value of the detection score, to cause a significant increase in diuresis, and wherein the delivered dose is titratable based on a measurement of a volume of the patient's brain.

2. The method of claim 1, wherein the delivered dose of loop diuretic causes no more than a 10% increase in a rate of the patient's urine production.

3. The method of claim 1, wherein the delivered dose of the loop diuretic compound is below a threshold to cause a significant decrease in an electrolyte level of the patient.

4. The method of claim 3, wherein the delivered dose of loop diuretic causes no more than a 5% decrease in a plasma concentration of the patient's potassium or sodium levels.

5. The method of claim 1, wherein the loop diuretic compound comprises furosemide.

6. The method of claim 5, wherein the dose of furosemide is less than that which causes the significant increase in diuresis.

7. The method of claim 5, wherein the dose of furosemide is in a range of 1 to 2000 µg.

8. The method of claim 7, wherein the dose of furosemide is in a range of 1 to 1000 µg.

9. The method of claim 7, wherein the dose of furosemide is in a range of 5 to 500 µg.

10. The method of claim 7, wherein the dose of furosemide is in a range of 10 to 250 µg.

11. The method of claim 7, wherein the dose of furosemide is in a range of 10 to 100 µg.

12. The method of claim 1, wherein the delivered dose of loop diuretic compound prevents or slows cortical spreading depression within the patient's brain.

13. The method of claim 1, wherein the delivered dose of loop diuretic blocks or slows ion flux within the patient's brain.

14. The method of claim 13, wherein the delivered dose of loop diuretic blocks or slows an ion pump co-transporter within glial cells of the patient's brain.

15. The method of claim 1, wherein the dose of loop diuretic compound is delivered into a ventricle in the patient's brain.

16. The method of claim 1, wherein the delivered dose of loop diuretic compound is delivered in a solid form which dissolves in the patient's brain.

17. The method of claim 1, wherein the detecting is performed using at least one electrode implanted in the patient's brain.

18. The method of claim 17, wherein the at least one electrode comprises three electrodes.

19. The method of claim 18, wherein the three electrodes have an orthogonal orientation with respect to each other.

20. The method of claim 1, wherein delivering the dose of loop diuretic comprises delivering a first dose, and further comprising delivering a second dose of loop diuretic compound.

21. The method of claim 20, wherein the second dose corresponds to a maintenance dose selected to prevent a re-occurrence of the pre-seizure or seizure event.

22. The method of claim 1, wherein each of the doses of loop diuretic compound attached to the belt are stored in individual packages attached to the belt.

23. The method of claim 22, wherein delivering the dose of the loop diuretic compound comprises removing the dose of the loop diuretic compound from the packaging, and advancing the dose of the loop diuretic compound through a delivery member to a delivery site in the brain.

24. The method of claim 23, wherein advancing the loop diuretic compound comprises pushing the dose through the delivery member by an advancement mechanism.

25. The method of claim 1, wherein the detection score further includes a time pattern of detection scores, the time pattern accounting for spikes in the detection score over a selected period of time.

26. A method for preventing or treating an epileptic seizure in a patient, the method comprising:
 storing doses of a loop diuretic compound in a subcutaneously implanted storage device, the storage device comprising a belt within the storage device to which the doses are attached;
 detecting an epileptic pre-seizure event or seizure event in the patient's brain, wherein detecting an epileptic pre-seizure or seizure includes generating a detection score; and
 delivering intra-cranially to the patient's brain, a dose of the loop diuretic compound from the belt to prevent or reduce a duration of the epileptic seizure, wherein the delivered dose of the loop diuretic compound is below a threshold, based on a value of the detection score, to cause a significant decrease in an electrolyte level of the patient, and wherein the delivered dose is titratable based on a measurement of a volume of the patient's brain.

27. The method of claim 26, wherein the delivered dose of loop diuretic compound causes no more than a 5% decrease in a plasma concentration of the patient's potassium or sodium levels.

28. The method of claim 26, wherein the loop diuretic compound comprises furosemide.

29. The method of claim 28, wherein the dose of furosemide is less than that which causes the significant decrease in the patient's electrolyte level.

30. The method of claim 28, wherein the dose of furosemide is in a range of 1 to 2000 µg.

31. The method of claim 26, wherein the detection score further includes a time pattern of detection scores, the time pattern accounting for spikes in the detection score over a selected period of time.

32. A method for preventing or treating in a patient a neural condition associated with cortical spreading depression, the method comprising:
 storing doses of a loop diuretic compound in a subcutaneously implanted storage device, the storage device comprising a belt within the storage device to which the doses are attached;
 detecting cortical spreading depression in the patient's brain, wherein detecting cortical spreading depression includes generating a detection score; and
 delivering intra-cranially to the patient's brain, a dose of the loop diuretic compound from the belt to prevent, slow or reduce a duration of cortical spreading depression, wherein the delivered dose of the loop diuretic compound is below a threshold, based on a value of the detection score, to cause significant amounts of diuresis, and wherein the delivered dose is titratable based on a measurement of a volume of the patient's brain.

33. The method of claim 32, wherein the detection score further includes a time pattern of detection scores, the time pattern accounting for spikes in the detection score over a selected period of time.

34. A method for preventing or treating an epileptic seizure in a patient, the method comprising:
 storing doses of a loop diuretic compound in a subcutaneously implanted storage device, the storage device comprising a belt to which the doses are attached;
 detecting an epileptic pre-seizure event or seizure event in the patient's brain, wherein detecting an epileptic pre-seizure or seizure includes generating a detection score; and
 delivering intra-cranially to the patient's brain, a dose of the loop diuretic compound from the belt to prevent or reduce a duration of the epileptic seizure, wherein the delivered dose of the loop diuretic compound, based on a value of the detection score, does not cause a significant physiological peripheral effect, and wherein the delivered dose is titratable based on a measurement of a volume of the patient's brain.

35. The method of claim 34, wherein the significant physiologic peripheral effect is an increase of more than 5% in a rate of the patient's urine production.

36. The method of claim 34, wherein the significant physiologic effect is a decrease of more than 5% in a plasma concentration of the patient's potassium or sodium levels.

37. The method of claim 34, wherein the detection score further includes a time pattern of detection scores, the time pattern accounting for spikes in the detection score over a selected period of time.

* * * * *